United States Patent
Liu et al.

(10) Patent No.: US 7,642,364 B2
(45) Date of Patent: Jan. 5, 2010

(54) BENZOPYRONE COMPOUNDS, PREPARATION METHOD AND USE THEREOF

(75) Inventors: Changling Liu, Shenyang (CN); Aiying Guan, Shenyang (CN); Hong Zhang, Shenyang (CN); Mingxing Zhang, Shenyang (CN); Zhengming Li, Shenyang (CN); Miao Li, Shenyang (CN); Lin Li, Shenyang (CN); Zhinian Li, Shenyang (CN); Chunqing Hou, Shenyang (CN)

(73) Assignee: Shenyang Research Institute of Chemical Industry, Shenyang (CN)

( * ) Notice: Subject to any disclaimer, the term of this patent is extended or adjusted under 35 U.S.C. 154(b) by 120 days.

(21) Appl. No.: 10/573,529

(22) PCT Filed: Nov. 4, 2004

(86) PCT No.: PCT/CN2004/001255

§ 371 (c)(1),
(2), (4) Date: Mar. 24, 2006

(87) PCT Pub. No.: WO2005/044813

PCT Pub. Date: May 19, 2005

(65) Prior Publication Data

US 2007/0037876 A1    Feb. 15, 2007

(30) Foreign Application Priority Data

Nov. 11, 2003   (CN) ................... 2003 1 0105079

(51) Int. Cl.
C07D 311/02   (2006.01)
(52) U.S. Cl. .................. 549/285; 549/283; 514/457
(58) Field of Classification Search ................ 549/285, 549/283; 514/457
See application file for complete search history.

(56) References Cited

U.S. PATENT DOCUMENTS

| | | | |
|---|---|---|---|
| 4,723,034 A | | 2/1988 | Schirmer et al. |
| 5,554,578 A | | 9/1996 | Wenderoth et al. |
| 6,034,121 A | * | 3/2000 | O'Mahony et al. .......... 514/456 |
| 6,906,007 B2 | * | 6/2005 | Fischer et al. ............... 504/292 |
| 2004/0102516 A1 | | 5/2004 | Fischer et al. |

FOREIGN PATENT DOCUMENTS

| | | |
|---|---|---|
| JP | 4-182461 | 6/1992 |
| JP | 04182461 A * | 6/1992 |
| WO | WO 01/98288 | 12/2001 |

OTHER PUBLICATIONS

International Preliminary Report on Patentability (PCT/IPEA/409) (Translated into English) for PCT/CN2004/001255.
Notification of Transmittal of Copies of Translation of the International Preliminary Report on Patentability issued for PCT/CN2004/001255 (Translated into English).

* cited by examiner

Primary Examiner—Daniel M Sullivan
Assistant Examiner—Sudhakar Katakam
(74) Attorney, Agent, or Firm—Smith, Gambrell & Russell, LLP

(57) ABSTRACT

The invention relates to pesticide and bactericide, specifically to the benzopyrone compounds and its preparation method and use thereof. The benzopyrone compounds of the invention having general formula (I):

(I)

[Chemical structure showing a benzopyrone compound with substituents $R_1$, $R_2$, $R_3$, $R_4$, $R_5$, $R_6$, $R_7$, $R_8$, A, B]

The present invention, having good pesticide activity and broad bactericide activity, applied for controlling various pests in plants such as army worm, diamond backmoth and aphid, carmine spider mite, two-spotted spider mite, ladybeetle, mites and mosquito larvae. Various disease in plants can be controlled by the invention and that of grape downy mildew, rice sheath and culm blight, rice blast, tomato early blight, tomato late blight, wheat leaf rust, wheat leaf blotch, wheat powdery mildew, cucumber powdery mildew, cucumber downy mildew, cucumber grey mold and so on.

4 Claims, No Drawings

BENZOPYRONE COMPOUNDS, PREPARATION METHOD AND USE THEREOF

FIELD OF THE INVENTION

The invention relates to insecticides and fungicides, specifically to benzopyrone compounds and its preparation method and use thereof.

BACKGROUND OF THE INVENTION

Benzopyrone and strobilurin (methoxyacrylate) compounds are natural products and known with biological active. Compounds of the following general formula have ever been published in JP04-182461:

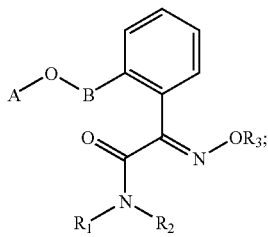

The structure of compound JP51 in JP04-182461 is as follows:

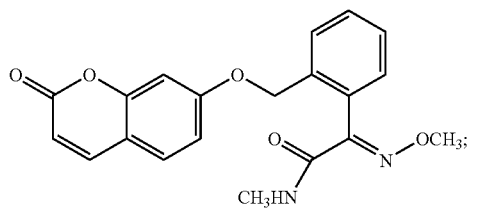

(JP51)

Biological active data of the compound in JP04-182461 have not been disclosed. After synthesis and the biological evaluation, it was found that compound JP51 has low biological active.

SUMMARY OF THE INVENTION

The aim of the present invention is to provide benzopyrone compounds with biological activity against all sorts of plant diseases and insects at very low dosage, and the compounds can be applied in agriculture to control diseases and insects in plant.

Detailed description of the invention is as follows:

The present invention offered benzopyrone compounds having general formula (I):

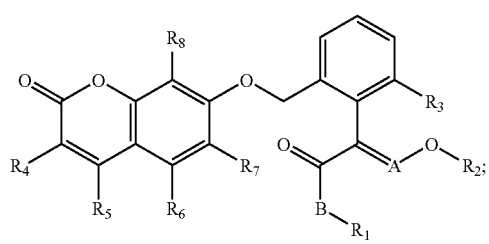

(I)

wherein: A is selected from CH or N;

B is selected from O, S or $NR_9$; $R_9$ is selected from H or $C_1$-$C_{12}$alkyl;

$R_1$ and $R_2$ are respectively selected from H, $C_1$-$C_{12}$alkyl or $C_1$-$C_{12}$ haloalkyl;

$R_3$ is selected from H, $C_1$-$C_{12}$alkyl, $C_1$-$C_{12}$ haloalkyl or $C_1$-$C_{12}$ alkoxy;

$R_4$, $R_5$, $R_6$, $R_7$, and $R_8$ may be the same or different, selected from H, halo, CN, $NO_2$, $C_1$-$C_{12}$alkyl, $C_2$-$C_{12}$alkenyl, $C_2$-$C_{12}$alkynyl, $C_1$-$C_{12}$haloalkyl, $C_1$-$C_{12}$alkoxy, $C_1$-$C_{12}$alkylthio, $C_1$-$C_{12}$alkylsulfonyl, $C_1$-$C_{12}$alkylcarbonyl, $C_1$-$C_{12}$alkoxy$C_1$-$C_{12}$alkyl, $C_1$-$C_{12}$alkoxycarbonyl, $C_1$-$C_{12}$alkoxycarbonyl $C_1$-$C_{12}$alkyl, $C_1$-$C_{12}$haloalkoxy$C_1$-$C_{12}$alkyl, or amino $C_1$-$C_{12}$alkyl in which amino is substituted with 0-2 $C_1$-$C_{12}$ alkyl, 0-3 substituted groups of aryl, aryloxyl, aryl$C_1$-$C_{12}$alkyl, aryl$C_1$-$C_{12}$alkoxy, aryloxy$C_1$-$C_{12}$alkyl, aryl$C_1$-$C_{12}$alkoxyl$C_1$-$C_{12}$alkyl, heteroaryl, heteroaryl$C_1$-$C_{12}$alkyl, or heteroaryl$C_1$-$C_{12}$alkoxyl, the 0-3 substituted groups may be selected from halo, $NO_2$, $C_1$-$C_6$alkyl, $C_1$-$C_6$haloalkyl, $C_1$-$C_6$alkoxy or $C_1$-$C_6$alkoxy$C_1$-$C_6$alkyl, and the groups having general formula are as follows:

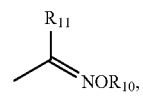

wherein: $R_{10}$ and $R_{11}$ are selected from H, $C_1$-$C_{12}$alkyl, aryl or aryl $C_1$-$C_{12}$alkyl; when $R_3$, $R_4$, $R_5$, $R_6$, $R_7$, and $R_8$ are all H, B is not $NR_9$;

and stereoisomer.

The preferred compounds of general formula (I) of this invention are:

A is selected from CH or N;

B is selected from O, S or $NR_9$; $R_9$ is selected from H or $C_1$-$C_6$alkyl;

$R_1$ and $R_2$ are respectively selected from H, $C_1$-$C_6$alkyl or $C_1$-$C_6$ haloalkyl;

$R_3$ is selected from H, $C_1$-$C_6$alkyl, $C_1$-$C_6$ haloalkyl or $C_1$-$C_6$alkoxy;

$R_4$, $R_5$, $R_6$, $R_7$, and $R_8$ may be the same or different, selected from H, halo, CN, $NO_2$, $C_1$-$C_6$alkyl, $C_2$-$C_6$alkenyl, $C_2$-$C_6$alkynyl, $C_1$-$C_6$haloalkyl, $C_1$-$C_6$alkoxy, $C_1$-$C_6$ alkylthio, $C_1$-$C_6$alkylsulfonyl, $C_1$-$C_6$alkylcarbonyl, $C_1$-$C_6$ alkoxy$C_1$-$C_6$alkyl, $C_1$-$C_6$alkoxycarbonyl, $C_1$-$C_6$alkoxycarbonyl$C_1$-$C_6$alkyl, $C_1$-$C_6$haloalkoxy$C_1$-$C_6$alkyl, or amino $C_1$-$C_6$alkyl in which amino is substituted with 0-2 $C_1$-$C_{12}$ alkyl, 0-3 substituted groups of aryl, aryloxyl, aryl$C_1$-$C_6$alkyl, aryl$C_1$-$C_6$alkoxy, aryloxy$C_1$-$C_6$alkyl, aryl$C_1$-$C_6$alkoxyl$C_1$-$C_6$alkyl, heteroaryl, heteroaryl$C_1$-$C_6$alkyl, heteroaryl$C_1$-$C_6$alkoxyl, the 0-3 substituted groups may be selected from halo, $NO_2$, $C_1$-$C_2$alkyl, $C_1$-$C_2$haloalkyl, $C_1$-$C_2$alkoxy or $C_1$-$C_2$alkoxy$C_1$-$C_2$alkyl, and groups having formula are as follows:

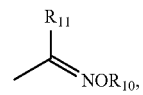

wherein: $R_{10}$ and $R_{11}$ are respectively selected from H, $C_1$-$C_{12}$alkyl, aryl or aryl$C_1$-$C_6$alkyl; when $R_3$, $R_4$, $R_5$, $R_6$, $R_7$, $R_8$ are all H, B is not $NR_9$;

Further more, the preferred compounds of general formula (I) of this invention are:

A is selected from CH or N;

B is selected from O or NH;

$R_1$ and $R_2$ are respectively selected from methyl;

$R_3$ is selected from H or methyl;

$R_4$, $R_5$, $R_6$, $R_7$, and $R_8$ may be the same or different, respectively selected from H, halo, CN, $NO_2$, $C_1$-$C_6$alkyl, $C_2$-$C_6$ alkenyl, $C_1$-$C_6$haloalkyl, $C_1$-$C_6$alkoxy, $C_1$-$C_6$alkylcarbonyl, $C_1$-$C_6$ alkoxy$C_1$-$C_6$alkyl, $C_1$-$C_6$alkoxycarbonyl, $C_1$-$C_6$alkoxycarbonyl$C_1$-$C_3$alkyl, $C_1$-$C_3$haloalkoxy$C_1$-$C_3$alkyl, or amino $C_1$-$C_3$alkyl in which amino is substituted with 0-2 $C_1$-$C_3$ alkyl, phenyl, phenoxy, phenyl$C_1$-$C_2$alkyl, phenyl$C_1$-$C_2$alkoxy, phenoxy$C_1$-$C_2$alkyl, phenylmethyl, phenylmethoxyl, or phenylmethoxy$C_1$-$C_2$alkyl substituted with 0-2 halo, $NO_2$, $C_1$-$C_2$alkyl, $C_1$-$C_2$haloalkyl, $C_1$-$C_2$alkoxy or $C_1$-$C_2$alkoxy$C_1$-$C_2$alkyl, and the substituted group having general formula is as follows:

$$\overset{R_{11}}{\underset{}{\diagdown}}{=}NOR_{10},$$

wherein: $R_{10}$ and $R_{11}$ are respectively selected from H or $C_1$-$C_6$alkyl; when $R_3$, $R_4$, $R_5$, $R_6$, $R_7$, and $R_8$ are all H, B is not NH.

Even more preferred compounds of formula (I) of this invention are:

A is selected from CH or N;

B is selected from O or NH;

$R_1$ and $R_2$ are selected from methyl;

$R_3$ is selected from H or methyl;

$R_4$, $R_5$, $R_6$, $R_7$, and $R_8$ may be the same or different, respectively selected from H, Cl, Br, F, CN, $C_1$-$C_6$alkyl, $C_1$-$C_6$haloalkyl, $C_1$-$C_6$alkylcarbonyl, Cl -$C_6$alkoxy, $C_1$-$C_6$alkoxy$C_1$-$C_3$alkyl, $C_1$-$C_3$haloalkoxy$C_1$-$C_3$alkyl, amino $C_1$-$C_3$alkyl in which amino is substituted with 0-2 $C_1$-$C_3$ alkyl, phenyl, phenoxy, phenylmethyl, phenylmethoxyl, substituted with 0-2 halo, $NO_2$, $C_1$-$C_2$alkyl, $C_1$-$C_2$haloalkyl, $C_1$-$C_2$alkoxy or $C_1$-$C_2$alkoxy$C_1$-$C_2$alkyl, and the substituted groups having general formula is as follows:

$$\overset{R_{11}}{\underset{}{\diagdown}}{=}NOR_{10},$$

wherein: $R_{10}$ and $R_{11}$ are selected from methyl; when $R_3$, $R_4$, $R_5$, $R_6$, $R_7$, $R_8$ are all H, B is not NH.

The following is the meaning of terms in the general formula (I):

Halogen or halo is meant to include fluoro, chloro, bromo or iodo.

The alkyl includes either straight or branched chain alkyl such as methyl, ethyl, propyl, isopropyl or tert-butyl.

The haloalkyl refers to straight or branched chain alkyl, in which hydrogen atom may be all or partly substituted with halogen, such as chloromethyl, dichloromethyl, trichloromethyl, fluoromethyl, difluoromethyl, or trifluoromethyl.

The alkoxy refers to straight or branched chain alkyl, which is linked to the structure by oxygen atom.

The haloalkoxy refers to straight or branched chain alkoxy, in which hydrogen atom may be all or partly substituted with halogen_, such as chloromethoxy, dichloromethoxy, trichloromethoxy, fluoromethoxy, difluoromethoxy, trifluoromethoxy, chlorofluoromethoxy, or trifluoroethoxy.

The alkenyl refers to an straight or branched, having double bonds at any position such as vinyl allyl. Substituted alkenyl includes arylvinyl which is substituted at any position with any group.

The alkynyl refers to straight or branched, having triple bonds at any position. such as ethynyl, propynyl. Substituted alkynyl includes arylethynyl which is substituted at any position with any group.

The aryl and aryl in arylalkyl, arylalkenyl, arylalkynyl, aryloxy, aryloxyalkyl include phenyl and naphthyl.

The substituent group in phenyl, phenoxy, phenylmethyl, phenylmethoxy are H, alkyl, alkoxy, haloalkyl, haloalkoxy, halo, $NO_2$, CN and the like. The number of the substituent group can be from one to five.

The hetero aryl in this invention refers to five member ring or six member ring containing one or many N, O, S hetero atom such as furan, thiophene, pyrrole, pyrazole, imidazole, thiazole, triazole, pyridine, pyrimidine, pyrazine, pyridazine, triazine, quinoline, benzofuran.

Because of the C=C and C=N link to different substituted group, the compounds of the invention may form geometrical isomer (the different isomers are respectively expressed with Z and E). Z isomer and E isomer and their mixture in any proportion are included in the invention.

The present invention is explained by the compounds of the following table I, but without being restricted thereby.

(I)

[structure of formula (I) showing a coumarin core with substituents $R_4$, $R_5$, $R_6$, $R_7$, $R_8$ and a side chain with $R_3$, $R_2$, $R_1$, A, B]

As provided in table 1, where $R_1$, $R_2$=$CH_3$; P is C($CH_3$)=NOCH$_3$; M is $C_6H_3$-3, 4-(OCH$_3$)$_2$.

TABLE 1

| No. | A | B | $R_3$ | $R_4$ | $R_5$ | $R_6$ | $R_7$ | $R_8$ | Physical-property* |
|---|---|---|---|---|---|---|---|---|---|
| 1 | CH | O | H | H | H | H | H | H | oil |
| 2 | CH | O | H | H | $CH_3$ | H | H | H | 140~143 |
| 3 | CH | O | H | H | $CH_3$ | H | H | $CH_3$ | 188–190 |
| 4 | CH | O | H | H | $C_6H_5$ | H | H | $CH_3$ | 146–148 |
| 5 | CH | O | H | $CH_3$ | $CH_3$ | H | H | H | 120–122 |
| 6 | CH | O | H | $CH_3$ | $CH_3$ | H | H | $CH_3$ | 174~176 |
| 7 | CH | O | H | H | $CF_3$ | H | H | H | 164~166 |
| 8 | CH | O | H | H | $CH_3$ | H | H | P | oil |
| 9 | CH | O | H | H | $CH_3$ | H | P | H | 183~185 |
| 10 | CH | O | H | H | $CH_3$ | H | $COCH_3$ | H | 169~172 |
| 11 | CH | O | H | H | $CH_3$ | H | H | $COCH_3$ | 165~167 |
| 12 | CH | O | H | Cl | $CH_3$ | H | H | H | 162–164 |
| 13 | CH | O | H | H | $CH_2Cl$ | H | H | H | |
| 14 | CH | O | H | Cl | $CH_2Cl$ | H | H | H | |
| 15 | CH | O | H | Cl | $CH_2OCH_3$ | H | H | H | |
| 16 | CH | O | H | Cl | $CH_2CH_3$ | H | H | H | |
| 17 | CH | O | H | H | $CH_2CH_3$ | H | H | $CH_3$ | 154–156 |
| 18 | CH | O | H | $C_2H_5$ | $CH_3$ | H | H | H | 132–135 |
| 19 | CH | O | H | H | $CH_2OCH_3$ | H | H | H | 140–142 |
| 20 | CH | O | H | H | $CH_2OC_2H_5$ | H | H | H | |
| 21 | CH | O | H | Cl | $CH_2OC_2H_5$ | H | H | H | |
| 22 | CH | O | H | $OCH_3$ | $CH_2OCH_3$ | H | H | H | |
| 23 | CH | O | H | $N(CH_3)_2$ | $CH_3$ | H | H | H | |
| 24 | CH | O | H | CN | H | H | H | H | 166–168 |
| 25 | CH | O | H | Cl | $CH_3$ | H | H | $CH_3$ | 202–204 |
| 26 | CH | O | H | H | $CH(CH_3)_2$ | H | H | H | 128–130 |
| 27 | CH | O | H | $C_3H_7$ | $CH_3$ | H | H | H | 142–144 |
| 28 | CH | O | H | H | $tC_4H_9$ | H | H | H | |
| 29 | CH | O | H | H | $4\text{-Cl}-C_6H_4$ | H | H | H | 149–152 |
| 30 | CH | O | H | Cl | $4\text{-Cl}-C_6H_4$ | H | H | H | |
| 31 | CH | O | H | H | $4\text{-Cl}-C_6H_4$ | H | H | $CH_3$ | |
| 32 | CH | O | H | Cl | $C_6H_5$ | H | H | H | 142–144 |
| 33 | CH | O | H | H | $CH_2CH_3$ | H | H | H | 134–136 |
| 34 | CH | O | H | H | $CH_2C_2H_5$ | H | H | H | 118–120 |
| 35 | CH | O | H | H | $CH_2C_2H_5$ | H | H | $CH_3$ | 146–148 |
| 36 | CH | O | H | Cl | $CH_2C_2H_5$ | H | H | H | 118–120 |
| 37 | CH | O | H | $CH_3$ | $CH_2C_2H_5$ | H | H | H | 112–115 |
| 38 | CH | O | H | H | $4\text{-F}-C_6H_4$ | H | H | H | 132–134 |
| 39 | CH | O | H | Cl | $4\text{-F}-C_6H_4$ | H | H | H | |
| 40 | CH | O | H | H | $4\text{-F}-C_6H_4$ | H | H | $CH_3$ | |
| 41 | CH | O | H | H | $4\text{-CF}_3-C_6H_4$ | H | H | H | 161–162 |
| 42 | CH | O | H | Cl | $4\text{-CF}_3-C_6H_4$ | H | H | H | |
| 43 | CH | O | H | Cl | $CH_2N(CH_3)_2$ | H | H | H | |
| 44 | CH | O | H | $OCH_3$ | $C_2H_5$ | H | H | H | |
| 45 | CH | O | H | $OCH_3$ | $CH_3$ | H | H | H | |
| 46 | CH | O | H | $OC_2H_5$ | $CH_3$ | H | H | H | |
| 47 | CH | O | H | H | $CH_2OCH_2CF_3$ | H | H | H | |
| 48 | CH | O | H | Cl | $CH_2OCH_2CF_3$ | H | H | H | |
| 49 | CH | O | H | F | $CF_3$ | H | H | H | |
| 50 | CH | O | H | F | $CH_3$ | H | H | H | 163–164 |
| 51 | CH | O | H | H | $CH_2N(CH_3)_2$ | H | H | H | |
| 52 | CH | O | H | H | $C_6H_5$ | H | H | H | 130–133 |
| 53 | CH | O | H | Cl | Cl | H | H | H | |
| 54 | CH | O | H | F | Cl | H | H | H | |
| 55 | CH | O | H | H | $CH_2OCH_2C_6H_5$ | H | P | H | |
| 56 | CH | O | H | $OCH_3$ | $4\text{-Cl}-C_6H_5$ | H | H | H | |
| 57 | CH | O | H | F | $4\text{-Cl}-C_6H_5$ | H | H | H | |
| 58 | CH | O | H | H | M | H | H | H | 81–83 |
| 59 | CH | O | H | Cl | M | H | H | H | |
| 60 | CH | O | H | Cl | M | H | H | $CH_3$ | |
| 61 | CH | O | H | $CH_3S$ | $CH_3$ | H | H | H | |
| 62 | CH | O | H | $CH_3SO_2$ | $CH_3$ | H | H | H | |
| 63 | CH | O | H | F | F | H | H | H | |
| 64 | CH | O | H | $CH_3SO_2$ | Cl | H | H | H | |
| 65 | CH | O | H | H | $4\text{-NO}_2-C_6H_5$ | H | H | H | |
| 66 | CH | O | H | Cl | $4\text{-NO}_2-C_6H_5$ | H | H | H | |
| 67 | CH | O | H | H | $4\text{-NO}_2-C_6H_5$ | H | H | $CH_3$ | |
| 68 | CH | O | H | $PhCH_2$ | $CH_3$ | H | H | H | 159–162 |
| 69 | CH | O | H | $PhCH_2$ | $CH_3$ | H | H | $CH_3$ | |
| 70 | CH | O | H | $CF_3CH_2O$ | $C_3H_7$ | H | H | H | |
| 71 | CH | NH | H | $CH_3$ | $CH_3$ | H | H | H | |
| 72 | CH | NH | H | $CH_3$ | $CH_3$ | H | H | $CH_3$ | |

TABLE 1-continued

| No. | A | B | $R_3$ | $R_4$ | $R_5$ | $R_6$ | $R_7$ | $R_8$ | Physical-property* |
|---|---|---|---|---|---|---|---|---|---|
| 73 | CH | NH | H | OCH$_3$ | CF$_3$ | CH$_3$ | H | H | |
| 74 | CH | NH | H | OCH$_3$ | CH$_3$ | F | H | P | |
| 75 | CH | NH | H | H | CF$_3$ | H | H | CH$_3$ | |
| 76 | CH | NH | H | CH$_3$ | CH$_2$Cl | H | H | H | |
| 77 | CH | NH | H | CH$_3$ | CH$_2$Cl | H | H | CH$_3$ | |
| 78 | CH | NH | H | Cl | CH$_2$Cl | H | H | H | |
| 79 | CH | NH | H | H | M | Cl | H | P | |
| 80 | CH | NH | H | H | M | H | P | H | |
| 81 | CH | NH | H | H | M | H | COCH$_3$ | H | |
| 82 | CH | NH | H | H | M | H | H | COCH$_3$ | |
| 83 | CH | NH | H | Cl | CH$_2$OCH$_3$ | H | H | H | |
| 84 | CH | NH | H | H | 4-C$_6$H$_5$Cl | H | H | H | |
| 85 | CH | NH | H | H | 4-C$_6$H$_5$Cl | H | H | CH$_3$ | |
| 86 | CH | NH | H | H | CH$_2$OCH$_3$ | H | H | CH$_3$ | |
| 87 | CH | NH | H | CH$_3$ | CH$_2$OCH$_3$ | H | H | H | |
| 88 | CH | NH | H | CH$_3$ | CH$_2$OCH$_3$ | H | H | CH$_3$ | |
| 89 | CH | NH | H | H | CH$_2$OCH$_3$ | H | H | H | |
| 90 | CH | NH | H | H | CH$_2$OCH$_3$ | H | H | P | |
| 91 | CH | NH | H | H | CH$_2$OCH$_2$CF$_3$ | H | P | H | |
| 92 | CH | NH | H | H | CH$_2$N(CH$_3$)$_2$ | H | H | H | |
| 93 | CH | NH | H | H | CH$_2$OCH$_2$CF$_3$ | H | H | COCH$_3$ | |
| 94 | CH | NH | H | Cl | CH$_2$OC$_2$H$_5$ | H | H | H | |
| 95 | CH | NH | H | H | CH$_2$OC$_2$H$_5$ | H | H | H | |
| 96 | CH | NH | H | H | CH$_2$OC$_2$H$_5$ | H | H | CH$_3$ | |
| 97 | CH | NH | H | H | CF$_3$ | H | H | CH$_3$ | |
| 98 | CH | NH | H | CH$_3$ | CF$_3$ | H | H | H | |
| 99 | CH | NH | H | CH$_3$ | Cl | H | H | CH$_3$ | |
| 100 | N | O | H | Cl | CH$_3$ | H | H | H | 172–174 |
| 101 | N | O | H | H | CH$_3$ | H | H | H | 150~152 |
| 102 | N | O | H | H | CH$_3$ | H | H | CH$_3$ | 178–180 |
| 103 | N | O | H | CH$_3$ | CH$_3$ | H | H | H | 112~118 |
| 104 | N | O | H | F | CH$_3$ | H | H | H | |
| 105 | N | O | H | H | CF$_3$ | H | H | Cl | |
| 106 | N | O | H | CH$_3$ | CH$_3$ | H | H | CH$_3$ | 184~186 |
| 107 | N | O | H | H | CH$_3$ | H | P | CO$_2$CH$_3$ | |
| 108 | N | O | H | H | CH$_3$ | H | COCH$_3$ | CO$_2$CH$_3$ | |
| 109 | N | O | H | Cl | CH$_3$ | H | H | CH$_3$ | 198–200 |
| 110 | N | O | H | H | CH$_2$Cl | H | H | CO$_2$CH$_3$ | |
| 111 | N | O | H | H | H | H | H | H | 106~110 |
| 112 | N | O | H | H | CH$_2$Cl | H | H | CF$_3$ | |
| 113 | N | O | H | H | 3-CF$_3$—C$_6$H$_4$ | H | H | CF$_3$ | |
| 114 | N | O | H | CH$_3$ | 3-CH$_3$—C$_6$H$_4$ | H | H | CF$_3$ | |
| 115 | N | O | H | CH$_3$ | 4-CH$_3$—C$_6$H$_4$ | H | H | CF$_3$ | |
| 116 | N | O | H | H | CH$_2$Cl | H | H | H | |
| 117 | N | O | H | Cl | CH$_2$Cl | H | H | H | |
| 118 | N | O | H | Cl | CH$_2$F | H | H | H | |
| 119 | N | O | H | H | CH$_2$F | H | H | H | |
| 120 | N | O | H | H | CH$_2$Br | H | H | H | |
| 121 | N | O | H | H | CH$_2$OCH$_3$ | H | H | CH$_2$N(CH$_3$)$_2$ | |
| 122 | N | O | H | Cl | CH$_2$OCH$_3$ | H | H | CH$_2$N(CH$_3$)$_2$ | |
| 123 | N | O | H | CH$_3$ | CH$_2$OCH$_3$ | H | H | CH$_2$N(CH$_3$)$_2$ | |
| 124 | N | O | H | H | CH$_2$OCH$_3$ | H | H | F | |
| 125 | N | O | H | CH$_3$ | CH$_2$OCH$_3$ | H | H | F | |
| 126 | N | O | H | CH$_3$ | CH$_2$OCH$_3$ | H | CO$_2$CH$_3$ | CH$_2$N(CH$_3$)$_2$ | |
| 127 | N | O | H | H | CH$_2$OCH$_3$ | H | H | H | |
| 128 | N | O | H | H | CH$_2$OCH$_3$ | H | H | P | |
| 129 | N | O | H | H | 3-CF$_3$—C$_6$H$_4$ | H | P | H | |
| 130 | N | O | H | H | 3-CH$_3$—C$_6$H$_4$ | H | COCH$_3$ | H | |
| 131 | N | O | H | H | 4-CH$_3$—C$_6$H$_4$ | H | H | COCH$_3$ | |
| 132 | N | O | H | Cl | CH$_2$OC$_2$H$_5$ | H | H | H | |
| 133 | N | O | H | H | CH$_2$OC$_2$H$_5$ | H | H | H | |
| 134 | N | O | H | H | CH$_2$OC$_2$H$_5$ | H | H | CH$_3$ | |
| 135 | N | O | H | H | 3-OCH$_3$—C$_6$H$_4$ | H | H | CH$_3$ | |
| 136 | N | O | H | CH$_3$ | 4-OCH$_3$—C$_6$H$_4$ | H | H | H | |
| 137 | N | O | H | CH$_3$ | 2-OCH$_3$—C$_6$H$_4$ | H | H | CH$_3$ | |
| 138 | N | O | H | H | CH$_2$OC$_2$H$_5$ | H | H | Cl | |
| 139 | N | O | H | H | CH$_2$OC$_2$H$_5$ | H | H | P | |
| 140 | N | O | H | H | M | H | P | H | |
| 141 | N | O | H | H | 3-CF$_3$—C$_6$H$_4$ | H | COCH$_3$ | H | |
| 142 | N | O | H | H | 3-CH$_3$—C$_6$H$_4$ | H | H | COCH$_3$ | |
| 143 | N | O | H | H | 4-CH$_3$—C$_6$H$_4$ | H | H | H | |
| 144 | N | O | H | H | 2-Cl—C$_6$H$_4$ | H | H | H | |
| 145 | N | O | H | H | 3-Cl—C$_6$H$_4$ | H | H | CH$_3$ | |
| 146 | N | O | H | H | CH$_2$OCH$_2$CF$_3$ | H | H | CH$_3$ | |
| 147 | N | O | H | CH$_3$ | CH$_2$OCH$_2$CF$_3$ | H | H | H | |
| 148 | N | O | H | CH$_3$ | —CH$_2$OC$_6$H$_5$ | H | H | CH$_3$ | |

TABLE 1-continued

| No. | A | B | $R_3$ | $R_4$ | $R_5$ | $R_6$ | $R_7$ | $R_8$ | Physical-property* |
|---|---|---|---|---|---|---|---|---|---|
| 149 | N | O | H | H | —$CH_2OC_6H_5$ | H | H | H | |
| 150 | N | O | H | H | $CH_2OCH_2C_6H_5$ | H | H | P | |
| 151 | N | O | H | H | $CH_2OCH_2C_6H_5$ | H | P | H | |
| 152 | N | O | H | H | 4-Cl—$C_6H_4$ | H | $COCH_3$ | H | |
| 153 | N | NH | H | H | $CH_3$ | H | H | H | 210–214 |
| 154 | N | NH | H | $CH_3$ | $CH_3$ | H | H | $CH_3$ | 178~180 |
| 155 | N | NH | H | H | 2-Cl—$C_6H_4$ | H | H | $CH_3$ | |
| 156 | N | NH | H | $CH_3$ | 3-Cl—$C_6H_4$ | H | H | H | |
| 157 | N | NH | H | $CH_3$ | 4-Cl—$C_6H_4$ | H | H | $CH_3$ | |
| 158 | N | NH | H | Cl | $CH_2Cl$ | H | H | H | |
| 159 | N | NH | H | Cl | $CH_3$ | H | H | H | |
| 160 | N | NH | H | H | 3-$CF_3$—$C_6H_4$ | H | P | H | |
| 161 | N | NH | H | H | 3-$CH_3$—$C_6H_4$ | H | $COCH_3$ | H | |
| 162 | N | NH | H | H | 4-$CH_3$—$C_6H_4$ | H | H | $COCH_3$ | |
| 163 | N | NH | H | H | $CH_2OCH_3$ | H | H | H | |
| 164 | N | NH | H | H | 4-F—$C_6H_4$ | H | H | H | |
| 165 | N | NH | H | H | 2-F—$C_6H_4$ | H | H | $CH_3$ | |
| 166 | N | NH | H | H | $C_6H_3$-3,5($Cl$)$_2$ | H | H | $CH_3$ | |
| 167 | N | NH | H | $CH_3$ | 2-$OCH_3$—$C_6H_4$ | H | H | H | |
| 168 | N | NH | H | $CH_3$ | 2-$OCH_3$—$C_6H_4$ | H | H | $CH_3$ | |
| 169 | N | NH | H | Cl | $CH_2OCH_3$ | H | H | H | |
| 170 | N | NH | H | H | $CH_2OCH_3$ | H | H | P | |
| 171 | N | NH | H | H | 3,5($Cl$)$_2$—$C_6H_3$ | H | P | H | |
| 172 | N | NH | H | H | 2,4($Cl$)$_2$—$C_6H_3$ | H | H | H | |
| 173 | N | NH | H | H | 3,4($Cl$)$_2$—$C_6H_3$ | H | H | H | |
| 174 | N | NH | H | Cl | $CH_2OC_2H_5$ | H | H | H | |
| 175 | N | NH | H | H | $CH_2OC_2H_5$ | H | H | H | |
| 176 | N | NH | H | H | $CH_2OC_2H_5$ | H | H | $CH_3$ | |
| 177 | N | NH | H | H | $CF_3$ | H | H | $CH_3$ | |
| 178 | N | NH | H | $CH_3$ | $CF_3$ | H | H | H | |
| 179 | N | NH | H | $CH_3$ | Cl | H | H | $CH_3$ | |
| 180 | N | NH | H | H | Cl | H | H | H | |
| 181 | N | NH | H | H | $CH_3$ | H | H | Cl | |
| 182 | N | NH | H | H | $C_6H_5$ | H | H | Cl | |
| 183 | N | NH | H | $CH_3$ | $CH_3$ | H | H | F | |
| 184 | N | NH | H | $CH_3$ | $CH_3$ | H | H | H | |
| 185 | N | NH | H | H | $CF_3$ | H | H | Cl | |
| 186 | N | NH | H | $CH_3$ | 4-F—$C_6H_4$ | H | H | $CH_3$ | |
| 187 | N | NH | H | H | 2-F—$C_6H_4$ | H | P | $CO_2CH_3$ | |
| 188 | N | NH | H | H | 2-Cl—$C_6H_4$ | H | $COCH_3$ | $CO_2CH_3$ | |
| 189 | N | NH | H | H | 3-Cl—$C_6H_4$ | H | H | $CO_2CH_3$ | |
| 190 | N | NH | H | H | 4-Cl—$C_6H_4$ | H | H | $CO_2CH_3$ | |
| 191 | N | NH | H | H | $CH_2Cl$ | H | $CH_3$ | H | |
| 192 | N | NH | H | H | $CH_2Cl$ | H | $CO_2C_2H_5$ | $CF_3$ | |
| 193 | N | NH | H | H | $CH_2Cl$ | H | H | $CF_3$ | |
| 194 | N | NH | H | $CH_3$ | M | H | $CO_2C_2H_5$ | $CF_3$ | |
| 195 | N | NH | H | $CH_3$ | $CH_2Cl$ | H | H | $CF_3$ | |
| 196 | N | NH | H | H | $CH_2Cl$ | H | H | H | |
| 197 | N | NH | H | H | $CH_2Cl$ | H | H | P | |
| 198 | N | NH | H | H | $CH_2Cl$ | H | P | H | |
| 199 | N | NH | H | H | $CH_2Cl$ | H | $COCH_3$ | H | |
| 200 | N | NH | H | $CH_3$ | 3,5-diCl—$C_6H_3$ | H | $CO_2CH_3$ | H | |
| 201 | CH | O | $CH_3$ | H | H | H | H | H | |
| 202 | CH | O | $CH_3$ | H | $CH_3$ | H | H | H | |
| 203 | CH | O | $CH_3$ | H | $CH_3$ | H | H | $CH_3$ | |
| 204 | CH | O | $CH_3$ | H | $C_6H_5$ | H | H | $CH_3$ | |
| 205 | CH | O | $CH_3$ | $CH_3$ | $CH_3$ | H | H | H | |
| 206 | CH | O | $CH_3$ | $CH_3$ | $CH_3$ | H | H | $CH_3$ | |
| 207 | CH | O | $CH_3$ | H | $CF_3$ | H | H | H | |
| 208 | CH | O | $CH_3$ | H | $CH_3$ | H | H | P | |
| 209 | CH | O | $CH_3$ | H | $CH_3$ | H | P | H | |
| 210 | CH | O | $CH_3$ | H | $CH_3$ | H | $COCH_3$ | H | |
| 211 | CH | O | $CH_3$ | H | $CH_3$ | H | H | $COCH_3$ | |
| 212 | CH | O | $CH_3$ | H | $CH_2Cl$ | H | H | H | |
| 213 | CH | O | $CH_3$ | Cl | $CH_2Cl$ | H | H | H | |
| 214 | CH | O | $CH_3$ | H | $CH_2Cl$ | H | H | $CF_3$ | |
| 215 | CH | O | $CH_3$ | H | $CH_2Cl$ | H | H | $CH_3$ | |
| 216 | CH | O | $CH_3$ | $CH_3$ | $CH_2OCH_3$ | H | H | H | |
| 217 | CH | O | $CH_3$ | $CH_3$ | $CH_2OCH_3$ | H | H | $CH_3$ | |
| 218 | CH | O | $CH_3$ | $OCH_3$ | $CH_2Cl$ | H | H | H | |
| 219 | CH | O | $CH_3$ | H | $CH_2Cl$ | H | H | P | |
| 220 | CH | O | $CH_3$ | H | $CH_2Cl$ | H | P | H | |
| 221 | CH | O | $CH_3$ | H | $CH_2Cl$ | H | $COCH_3$ | H | |
| 222 | CH | O | $CH_3$ | H | $CH_2Cl$ | H | H | COCH3 | |
| 223 | CH | O | $CH_3$ | H | $CH_2OCH_2CF_3$ | H | H | H | |
| 224 | CH | O | $CH_3$ | Cl | $CH_2OC_2H_5$ | H | H | H | |

TABLE 1-continued

| No. | A | B | $R_3$ | $R_4$ | $R_5$ | $R_6$ | $R_7$ | $R_8$ | Physical-property* |
|---|---|---|---|---|---|---|---|---|---|
| 225 | CH | O | $CH_3$ | Cl | $CH_2OCH_3$ | H | H | $CH_3$ | |
| 226 | CH | O | $CH_3$ | H | $CH_2OCH_3$ | H | H | $CH_3$ | |
| 227 | CH | O | $CH_3$ | $CH_3$ | 3-$CF_3$—$C_6H_4$ | H | H | H | |
| 228 | CH | O | $CH_3$ | $CH_3$ | 3-$CH_3$—$C_6H_4$ | H | H | $CH_3$ | |
| 229 | CH | O | $CH_3$ | H | 4-$CH_3$—$C_6H_4$ | H | H | H | |
| 230 | CH | O | $CH_3$ | H | 2-Cl—$C_6H_4$ | H | H | P | |
| 231 | CH | O | $CH_3$ | H | 3-Cl—$C_6H_4$ | H | P | H | |
| 232 | CH | O | $CH_3$ | H | $CF_3$ | H | $COCH_3$ | H | |
| 233 | CH | O | $CH_3$ | Cl | $CH_2OCH_3$ | H | H | $COCH_3$ | |
| 234 | CH | O | $CH_3$ | $OCH_3$ | $CH_2OC_2H_5$ | H | H | H | |
| 235 | CH | O | $CH_3$ | $C_2H_5$ | $CH_2OC_2H_5$ | H | $CH_3$ | H | |
| 236 | CH | O | $CH_3$ | H | $CH_2OC_2H_5$ | H | H | $CH_3$ | |
| 237 | CH | O | $CH_3$ | Cl | $CH_2OC_2H_5$ | H | $CO_2C_2H_5$ | $CH_3$ | |
| 238 | CH | O | $CH_3$ | $CH_3$ | 2-F—$C_6H_4$ | H | H | H | |
| 239 | CH | O | $CH_3$ | $CH_3$ | 3-F—$C_6H_4$ | H | H | $CH_3$ | |
| 240 | CH | O | $CH_3$ | H | 4-F—$C_6H_4$ | H | H | H | |
| 241 | CH | O | $CH_3$ | H | $CH_2OC_2H_5$ | H | H | P | |
| 242 | CH | O | $CH_3$ | H | $CH_2OC_2H_5$ | H | P | H | |
| 243 | CH | O | $CH_3$ | H | $CH_2OC_2H_5$ | H | $COCH_3$ | H | |
| 244 | CH | O | $CH_3$ | H | $CH_2OC_2H_5$ | H | H | $COCH_3$ | |
| 245 | CH | O | $CH_3$ | H | $CH_2OCH_2CF_3$ | H | H | H | |
| 246 | CH | O | $CH_3$ | Cl | $CH_2OCH_2CF_3$ | H | H | H | |
| 247 | CH | O | $CH_3$ | H | $CF_3$ | H | H | $CH_3$ | |
| 248 | CH | O | $CH_3$ | H | $CH_2OCH_2CF_3$ | H | H | $CH_3$ | |
| 249 | CH | O | $CH_3$ | $CH_3$ | $CH_2OCH_2CF_3$ | H | H | H | |
| 250 | CH | O | $CH_3$ | $CH_3$ | —$CH_2$OPh | H | H | $CH_3$ | |
| 251 | CH | O | $CH_3$ | H | —$CH_2$OPh | H | H | H | |
| 252 | CH | O | $CH_3$ | H | $CH_2OCH_2$Ph | H | H | P | |
| 253 | CH | O | $CH_3$ | H | $CH_2OCH_2$Ph | H | P | H | |
| 254 | CH | O | $CH_3$ | H | 4-Cl—$C_6H_5$ | H | $COCH_3$ | H | |
| 255 | CH | O | $CH_3$ | H | 4-Cl—$C_6H_5$ | H | H | $COCH_3$ | |
| 256 | CH | O | $CH_3$ | H | M | H | $CO_2C_2H_5$ | H | |
| 257 | CH | O | $CH_3$ | H | M | H | H | H | |
| 258 | CH | O | $CH_3$ | Cl | M | H | H | $CH_3$ | |
| 259 | CH | O | $CH_3$ | H | M | H | H | $CH_3$ | |
| 260 | CH | O | $CH_3$ | $CH_3$ | M | H | H | H | |
| 261 | CH | NH | $CH_3$ | Cl | H | H | H | H | |
| 262 | CH | NH | $CH_3$ | Cl | $CH_3$ | H | H | H | |
| 263 | CH | NH | $CH_3$ | H | $CH_3$ | H | H | $CH_3$ | |
| 264 | CH | NH | $CH_3$ | H | $C_6H_5$ | H | H | $CH_3$ | |
| 265 | CH | NH | $CH_3$ | $CH_3$ | $CH_3$ | H | H | H | |
| 266 | CH | NH | $CH_3$ | $CH_3$ | $CH_3$ | H | H | $CH_3$ | |
| 267 | CH | NH | $CH_3$ | $OCH_3$ | $CF_3$ | H | H | H | |
| 268 | CH | NH | $CH_3$ | $OCH_3$ | $CH_3$ | H | H | P | |
| 269 | CH | NH | $CH_3$ | H | $CH_3$ | H | P | H | |
| 270 | CH | NH | $CH_3$ | H | $CH_3$ | H | $COCH_3$ | H | |
| 271 | CH | NH | $CH_3$ | H | $CH_3$ | H | H | $COCH_3$ | |
| 272 | CH | NH | $CH_3$ | H | $CH_2Cl$ | H | H | H | |
| 273 | CH | NH | $CH_3$ | H | M | H | H | H | |
| 274 | CH | NH | $CH_3$ | H | $CH_2Cl$ | H | H | $CH_3$ | |
| 275 | CH | NH | $CH_3$ | H | $CF_3$ | H | H | $CH_3$ | |
| 276 | CH | NH | $CH_3$ | $CH_3$ | $CH_2Cl$ | H | H | H | |
| 277 | CH | NH | $CH_3$ | $CH_3$ | $CH_2Cl$ | H | H | $CH_3$ | |
| 278 | CH | NH | $CH_3$ | Cl | $CH_2Cl$ | H | H | H | |
| 279 | CH | NH | $CH_3$ | H | M | H | H | P | |
| 280 | CH | NH | $CH_3$ | H | M | H | P | H | |
| 281 | CH | NH | $CH_3$ | H | M | H | $COCH_3$ | H | |
| 282 | CH | NH | $CH_3$ | H | M | H | H | $COCH_3$ | |
| 283 | CH | NH | $CH_3$ | Cl | $CH_2OCH_3$ | H | H | H | |
| 284 | CH | NH | $CH_3$ | H | 4-$C_6H_5$Cl | H | H | H | |
| 285 | CH | NH | $CH_3$ | H | 4-$C_6H_5$Cl | H | H | $CH_3$ | |
| 286 | CH | NH | $CH_3$ | H | $CH_2OCH_3$ | H | H | $CH_3$ | |
| 287 | CH | NH | $CH_3$ | $CH_3$ | $CH_2OCH_3$ | H | H | H | |
| 288 | CH | NH | $CH_3$ | $CH_3$ | $CH_2OCH_3$ | H | H | $CH_3$ | |
| 289 | CH | NH | $CH_3$ | H | $CH_2OCH_3$ | H | H | H | |
| 290 | CH | NH | $CH_3$ | H | $CH_2OCH_3$ | H | H | P | |
| 291 | CH | NH | $CH_3$ | H | $CH_2OCH_2CF_3$ | H | P | H | |
| 292 | CH | NH | $CH_3$ | H | $CH_2OCH_2CF_3$ | H | $COCH_3$ | H | |
| 293 | CH | NH | $CH_3$ | H | $CH_2OCH_2CF_3$ | H | H | $COCH_3$ | |
| 294 | CH | NH | $CH_3$ | Cl | $CH_2OC_2H_5$ | H | H | H | |
| 295 | CH | NH | $CH_3$ | H | $CH_2OC_2H_5$ | H | H | H | |
| 296 | CH | NH | $CH_3$ | H | $CH_2OC_2H_5$ | H | H | $CH_3$ | |
| 297 | CH | NH | $CH_3$ | H | $CF_3$ | H | H | $CH_3$ | |
| 298 | CH | NH | $CH_3$ | $CH_3$ | $CF_3$ | H | H | H | |
| 299 | CH | NH | $CH_3$ | $CH_3$ | Cl | H | H | $CH_3$ | |
| 300 | CH | NH | $CH_3$ | H | Cl | H | H | H | |

TABLE 1-continued

| No. | A | B | R₃ | R₄ | R₅ | R₆ | R₇ | R₈ | Physical-property* |
|---|---|---|---|---|---|---|---|---|---|
| 301 | N | O | CH₃ | H | CH₃ | H | H | H | |
| 302 | N | O | CH₃ | H | C₆H₅ | H | H | Cl | |
| 303 | N | O | CH₃ | CH₃ | CH₃ | H | H | H | |
| 304 | N | O | CH₃ | CH₃ | CH₃ | H | H | H | |
| 305 | N | O | CH₃ | H | CF₃ | H | H | Cl | |
| 306 | N | O | CH₃ | CH₃ | CH₃ | H | H | CH₃ | |
| 307 | N | O | CH₃ | H | CH₃ | H | P | CO₂CH₃ | |
| 308 | N | O | CH₃ | H | CH₃ | H | COCH₃ | CO₂CH₃ | |
| 309 | N | O | CH₃ | H | CH₃ | H | H | CO₂CH₃ | |
| 310 | N | O | CH₃ | H | CH₂Cl | H | H | CO₂CH₃ | |
| 311 | N | O | CH₃ | H | H | H | H | H | |
| 312 | N | O | CH₃ | H | CH₂Cl | H | H | CF₃ | |
| 313 | N | O | CH₃ | H | 3-CF₃—C₆H₄ | H | H | CF₃ | |
| 314 | N | O | CH₃ | CH₃ | 3-CH₃—C₆H₄ | H | H | CF₃ | |
| 315 | N | O | CH₃ | CH₃ | 4-CH₃—C₆H₄ | H | H | CF₃ | |
| 316 | N | O | CH₃ | H | CH₂Cl | H | H | H | |
| 317 | N | O | CH₃ | H | CH₂Cl | H | H | P | |
| 318 | N | O | CH₃ | H | CH₂Cl | H | P | H | |
| 319 | N | O | CH₃ | H | CH₂Cl | H | COCH₃ | H | |
| 320 | N | O | CH₃ | H | CH₂Cl | H | H | COCH3 | |
| 321 | N | O | CH₃ | H | CH₂OCH₃ | H | H | CH₂N(CH₃)₂ | |
| 322 | N | O | CH₃ | Cl | CH₂OCH₃ | H | H | CH₂N(CH₃)₂ | |
| 323 | N | O | CH₃ | CH₃ | CH₂OCH₃ | H | H | CH₂N(CH₃)₂ | |
| 324 | N | O | CH₃ | H | CH₂OCH₃ | H | H | F | |
| 325 | N | O | CH₃ | CH₃ | CH₂OCH₃ | H | H | F | |
| 326 | N | O | CH₃ | CH₃ | CH₂OCH₃ | H | CO₂CH₃ | CH₂N(CH₃)₂ | |
| 327 | N | O | CH₃ | H | CH₂OCH₃ | H | H | H | |
| 328 | N | O | CH₃ | H | CH₂OCH₃ | H | H | P | |
| 329 | N | O | CH₃ | H | 3-CF₃—C₆H₄ | H | P | H | |
| 330 | N | O | CH₃ | H | 3-CH₃—C₆H₄ | H | COCH₃ | H | |
| 331 | N | O | CH₃ | H | 4-CH₃—C₆H₄ | H | H | COCH₃ | |
| 332 | N | O | CH₃ | Cl | CH₂OC₂H₅ | H | H | H | |
| 333 | N | O | CH₃ | H | CH₂OC₂H₅ | H | H | H | |
| 334 | N | O | CH₃ | H | CH₂OC₂H₅ | H | H | CH₃ | |
| 335 | N | O | CH₃ | H | 3-OCH₃—C₆H₄ | H | H | CH₃ | |
| 336 | N | O | CH₃ | CH₃ | 4-OCH₃—C₆H₄ | H | H | H | |
| 337 | N | O | CH₃ | CH₃ | 2-OCH₃—C₆H₄ | H | H | CH₃ | |
| 338 | N | O | CH₃ | H | CH₂OC₂H₅ | H | H | Cl | |
| 339 | N | O | CH₃ | H | CH₂OC₂H₅ | H | H | P | |
| 340 | N | O | CH₃ | H | M | H | P | H | |
| 341 | N | O | CH₃ | H | 3-CF₃—C₆H₄ | H | COCH₃ | H | |
| 342 | N | O | CH₃ | H | 3-CH₃—C₆H₄ | H | H | COCH₃ | |
| 343 | N | O | CH₃ | H | 4-CH₃—C₆H₄ | H | H | H | |
| 344 | N | O | CH₃ | H | 2-Cl—C₆H₄ | H | H | H | |
| 345 | N | O | CH₃ | H | 3-Cl—C₆H₄ | H | H | CH₃ | |
| 346 | N | O | CH₃ | H | CH₂OCH₂CF₃ | H | H | CH₃ | |
| 347 | N | O | CH₃ | CH₃ | CH₂OCH₂CF₃ | H | H | H | |
| 348 | N | O | CH₃ | CH₃ | —CH₂OPh | H | H | CH₃ | |
| 349 | N | O | CH₃ | H | —CH₂OPh | H | H | H | |
| 350 | N | O | CH₃ | H | CH₂OCH₂Ph | H | H | P | |
| 351 | N | O | CH₃ | H | CH₂OCH₂Ph | H | P | H | |
| 352 | N | O | CH₃ | H | 4-Cl—C₆H₄ | H | COCH₃ | H | |
| 353 | N | NH | CH₃ | H | CH₃ | H | H | H | |
| 354 | N | NH | CH₃ | CH₃ | CH₃ | H | H | CH₃ | |
| 355 | N | NH | CH₃ | H | 2-Cl—C₆H₄ | H | H | CH₃ | |
| 356 | N | NH | CH₃ | CH₃ | 3-Cl—C₆H₄ | H | H | H | |
| 357 | N | NH | CH₃ | CH₃ | 4-Cl—C₆H₄ | H | H | CH₃ | |
| 358 | N | NH | CH₃ | H | CH₂Cl | H | H | H | |
| 359 | N | NH | CH₃ | H | M | H | H | P | |
| 360 | N | NH | CH₃ | H | 3-CF₃—C₆H₄ | H | P | H | |
| 361 | N | NH | CH₃ | H | 3-CH₃—C₆H₄ | H | COCH₃ | H | |
| 362 | N | NH | CH₃ | H | 4-CH₃—C₆H₄ | H | H | COCH₃ | |
| 363 | N | NH | CH₃ | H | CH₂OCH₃ | H | H | H | |
| 364 | N | NH | CH₃ | H | 4-F—C₆H₄ | H | H | H | |
| 365 | N | NH | CH₃ | H | 2-F—C₆H₄ | H | H | CH₃ | |
| 366 | N | NH | CH₃ | H | C₆H₃-3,5(Cl)₂ | H | H | CH₃ | |
| 367 | N | NH | CH₃ | CH₃ | 2-OCH₃—C₆H₄ | H | H | H | |
| 368 | N | NH | CH₃ | CH₃ | 2-OCH₃—C₆H₄ | H | H | CH₃ | |

TABLE 1-continued

| No. | A | B | $R_3$ | $R_4$ | $R_5$ | $R_6$ | $R_7$ | $R_8$ | Physical-property* |
|---|---|---|---|---|---|---|---|---|---|
| 369 | N | NH | $CH_3$ | Cl | $CH_2OCH_3$ | H | H | H | |
| 370 | N | NH | $CH_3$ | H | $CH_2OCH_3$ | H | H | P | |
| 371 | N | NH | $CH_3$ | H | $C_6H_3$-3,5$(Cl)_2$ | H | P | H | |
| 372 | N | NH | $CH_3$ | H | $CH_2OCH_2CF_3$ | H | $COCH_3$ | H | |
| 373 | N | NH | $CH_3$ | H | $CH_2OCH_2CF_3$ | H | H | $COCH_3$ | |
| 374 | N | NH | $CH_3$ | Cl | $CH_2OC_2H_5$ | H | H | H | |
| 375 | N | NH | $CH_3$ | H | $CH_2OC_2H_5$ | H | H | H | |
| 376 | N | NH | $CH_3$ | H | $CH_2OC_2H_5$ | H | H | $CH_3$ | |
| 377 | N | NH | $CH_3$ | H | $CF_3$ | H | H | $CH_3$ | |
| 378 | N | NH | $CH_3$ | $CH_3$ | $CF_3$ | H | H | H | |
| 379 | N | NH | $CH_3$ | $CH_3$ | Cl | H | H | $CH_3$ | |
| 380 | N | NH | $CH_3$ | H | Cl | H | H | H | |
| 381 | N | NH | $CH_3$ | H | $CH_3$ | H | H | Cl | |
| 382 | N | NH | $CH_3$ | H | $C_6H_5$ | H | H | Cl | |
| 383 | N | NH | $CH_3$ | $CH_3$ | $CH_3$ | H | H | F | |
| 384 | N | NH | $CH_3$ | $CH_3$ | $CH_3$ | H | H | H | |
| 385 | N | NH | $CH_3$ | H | $CF_3$ | H | H | Cl | |
| 386 | N | NH | $CH_3$ | $CH_3$ | 4-F—$C_6H_4$ | H | H | $CH_3$ | |
| 387 | N | NH | $CH_3$ | H | 2-F—$C_6H_4$ | H | P | $CO_2CH_3$ | |
| 388 | N | NH | $CH_3$ | H | 2-Cl—$C_6H_4$ | H | $COCH_3$ | $CO_2CH_3$ | |
| 389 | N | NH | $CH_3$ | H | 3-Cl—$C_6H_4$ | H | H | $CO_2CH_3$ | |
| 390 | N | NH | $CH_3$ | H | 4-Cl—$C_6H_4$ | H | H | $CO_2CH_3$ | |
| 391 | N | NH | $CH_3$ | H | $CH_2Cl$ | H | $CH_3$ | H | |
| 392 | N | NH | $CH_3$ | H | $CH_2Cl$ | H | $CO_2C_2H_5$ | $CF_3$ | |
| 393 | N | NH | $CH_3$ | H | $CH_2Cl$ | H | H | $CF_3$ | |
| 394 | N | NH | $CH_3$ | $CH_3$ | M | H | $CO_2C_2H_5$ | $CF_3$ | |
| 395 | N | NH | $CH_3$ | $CH_3$ | $CH_2Cl$ | H | H | $CF_3$ | |
| 396 | N | NH | $CH_3$ | H | $CH_2Cl$ | H | H | H | |
| 397 | N | NH | $CH_3$ | H | $CH_2Cl$ | H | H | P | |
| 398 | N | NH | $CH_3$ | H | $CH_2Cl$ | H | P | H | |
| 399 | N | NH | $CH_3$ | H | $CH_2Cl$ | H | $COCH_3$ | H | |
| 400 | N | NH | $CH_3$ | $CH_3$ | 3,5-diCl—$C_6H_3$ | H | $CO_2CH_3$ | H | |
| 401 | CH | O | H | $C_3H_7i$ | $CH_3$ | H | H | H | oil |
| 402 | CH | O | H | n-$C_4H_9$ | $CH_3$ | H | H | H | 117–118 |
| 403 | CH | O | H | n-$C_5H_{11}$ | $CH_3$ | H | H | H | |
| 404 | CH | O | H | $C_2H_4$Pri | $CH_3$ | H | H | H | oil |
| 405 | CH | O | H | n-$C_6H_{13}$ | $CH_3$ | H | H | H | 113–115 |
| 406 | CH | O | H | H | n-$C_4H_9$ | H | H | H | |
| 407 | CH | O | H | H | n-$C_5H_{11}$ | H | H | H | |
| 408 | CH | O | H | H | $CH(CH_3)_2$ | H | H | $CH_3$ | 110–112 |
| 409 | CH | O | H | n-$C_3H_7$ | n-$C_3H_7$ | H | H | H | 112–114 |
| 410 | N | O | H | Cl | n-$C_3H_7$ | H | H | H | 136–138 |
| 411 | N | O | H | Cl | $C_6H_5$ | H | H | H | 166–168 |
| 412 | N | O | H | n-$C_3H_7$ | $CH_3$ | H | H | H | 121–122 |
| 413 | N | O | H | n-$C_4H_9$ | $CH_3$ | H | H | H | 100–102 |
| 414 | N | O | H | n-$C_6H_{13}$ | $CH_3$ | H | H | H | 75–78 |
| 415 | CH | O | H | $CH_3$ | n-$C_4H_9$ | H | H | H | |
| 416 | CH | O | H | $C_2H_5$ | n-$C_4H_9$ | H | H | H | |
| 417 | CH | O | H | $C_3H_7$ | n-$C_4H_9$ | H | H | H | |
| 418 | CH | O | H | i-$C_3H_7$ | n-$C_4H_9$ | H | H | H | |
| 419 | CH | O | H | n-$C_4H_9$ | n-$C_4H_9$ | H | H | H | |
| 420 | CH | O | H | $CH_3$ | n-$C_5H_{11}$ | H | H | H | |
| 421 | CH | O | H | $C_2H_5$ | n-$C_5H_{11}$ | H | H | H | |
| 422 | CH | O | H | $C_3H_7$ | n-$C_5H_{11}$ | H | H | H | |
| 423 | CH | O | H | i-$C_3H_7$ | n-$C_5H_{11}$ | H | H | H | |
| 424 | CH | O | H | n-$C_4H_9$ | n-$C_5H_{11}$ | H | H | H | |
| 425 | CH | O | H | H | n-$C_6H_{13}$ | H | H | H | |
| 426 | CH | O | H | $CH_3$ | n-$C_6H_{13}$ | H | H | H | |
| 427 | CH | O | H | $C_2H_5$ | n-$C_6H_{13}$ | H | H | H | |
| 428 | CH | O | H | $C_3H_7$ | n-$C_6H_{13}$ | H | H | H | |
| 429 | CH | O | H | i-$C_3H_7$ | n-$C_6H_{13}$ | H | H | H | |
| 430 | CH | O | H | n-$C_4H_9$ | n-$C_6H_{13}$ | H | H | H | |
| 431 | N | O | H | $CH_3$ | n-$C_4H_9$ | H | H | H | |
| 432 | N | O | H | $C_2H_5$ | n-$C_4H_9$ | H | H | H | |
| 433 | N | O | H | $C_3H_7$ | n-$C_4H_9$ | H | H | H | |
| 434 | N | O | H | i-$C_3H_7$ | n-$C_4H_9$ | H | H | H | |

TABLE 1-continued

| No. | A | B | $R_3$ | $R_4$ | $R_5$ | $R_6$ | $R_7$ | $R_8$ | Physical-property* |
|---|---|---|---|---|---|---|---|---|---|
| 435 | N | O | H | n-$C_4H_9$ | n-$C_4H_9$ | H | H | H | |
| 436 | N | O | H | $CH_3$ | n-$C_5H_{11}$ | H | H | H | |
| 437 | N | O | H | $C_2H_5$ | n-$C_5H_{11}$ | H | H | H | |
| 438 | N | O | H | $C_3H_7$ | n-$C_5H_{11}$ | H | H | H | |
| 439 | N | O | H | i-$C_3H_7$ | n-$C_5H_{11}$ | H | H | H | |
| 440 | N | O | H | n-$C_4H_9$ | n-$C_5H_{11}$ | H | H | H | |
| 441 | N | O | H | H | n-$C_6H_{13}$ | H | H | H | |
| 442 | N | O | H | $CH_3$ | n-$C_6H_{13}$ | H | H | H | |
| 443 | N | O | H | $C_2H_5$ | n-$C_6H_{13}$ | H | H | H | |
| 444 | N | O | H | $C_3H_7$ | n-$C_6H_{13}$ | H | H | H | |
| 445 | N | O | H | i-$C_3H_7$ | n-$C_6H_{13}$ | H | H | H | |
| 446 | N | O | H | n-$C_4H_9$ | n-$C_6H_{13}$ | H | H | H | |
| 447 | N | NH | H | $CH_3$ | n-$C_4H_9$ | H | H | H | |
| 448 | N | NH | H | $C_2H_5$ | n-$C_4H_9$ | H | H | H | |
| 449 | N | NH | H | $C_3H_7$ | n-$C_4H_9$ | H | H | H | |
| 450 | N | NH | H | i-$C_3H_7$ | n-$C_4H_9$ | H | H | H | |
| 451 | N | NH | H | n-$C_4H_9$ | n-$C_4H_9$ | H | H | H | |
| 452 | N | NH | H | $CH_3$ | n-$C_5H_{11}$ | H | H | H | |
| 453 | N | NH | H | $C_2H_5$ | n-$C_5H_{11}$ | H | H | H | |
| 454 | N | NH | H | $C_3H_7$ | n-$C_5H_{11}$ | H | H | H | |
| 455 | N | NH | H | i-$C_3H_7$ | n-$C_5H_{11}$ | H | H | H | |
| 456 | N | NH | H | n-$C_4H_9$ | n-$C_5H_{11}$ | H | H | H | |
| 457 | N | NH | H | H | n-$C_6H_{13}$ | H | H | H | |
| 458 | N | NH | H | $CH_3$ | n-$C_6H_{13}$ | H | H | H | |
| 459 | N | NH | H | $C_2H_5$ | n-$C_6H_{13}$ | H | H | H | |
| 460 | N | NH | H | $C_3H_7$ | n-$C_6H_{13}$ | H | H | H | |
| 461 | N | NH | H | i-$C_3H_7$ | n-$C_6H_{13}$ | H | H | H | |
| 462 | N | NH | H | n-$C_4H_9$ | n-$C_6H_{13}$ | H | H | H | |
| 463 | CH | O | H | H | $CH_2$-Ph-4-Cl | H | H | H | |
| 464 | CH | O | H | $CH_3$ | $CH_2$-Ph-4-Cl | H | H | H | |
| 465 | CH | O | H | $C_2H_5$ | $CH_2$-Ph-4-Cl | H | H | H | |
| 466 | CH | O | H | $CH_2$-Ph-4-Cl | $CH_3$ | H | H | H | |
| 467 | CH | O | H | $CH_2$-Ph-4-Cl | $C_2H_5$ | H | H | H | |
| 468 | CH | O | H | $CH_2$-Ph-4-Cl | $C_3H_7$ | H | H | H | |
| 469 | CH | O | H | $CH_3$ | $CF_3$ | H | H | H | |
| 470 | CH | O | H | Cl | $CF_3$ | H | H | H | |
| 471 | CH | O | H | $C_2H_5$ | $CF_3$ | H | H | H | |
| 472 | CH | O | H | n-$C_3H_7$ | $CF_3$ | H | H | H | |
| 473 | CH | O | H | n-$C_4H_9$ | $CF_3$ | H | H | H | |
| 474 | CH | O | H | H | $CH_2CH_2$-Ph-4-Cl | H | H | H | |
| 475 | CH | O | H | $CH_3$ | | H | H | H | |
| 476 | CH | O | H | H | $CH_2$Bu-t | H | H | H | |
| 477 | CH | O | H | $CH_3$ | $CH_2$Bu-t | H | H | H | |
| 478 | CH | O | H | n-$C_3H_7$ | $CH_2$Bu-t | H | H | H | |
| 479 | CH | O | H | $CH_2$Bu-t | $CH_3$ | H | H | H | |
| 480 | CH | O | H | $CH_2CH_2$-Ph-4-Cl | $CH_3$ | H | H | H | |
| 481 | CH | O | H | | $C_2H_5$ | H | H | H | |
| 482 | CH | O | H | | $C_3H_7$ | H | H | H | |
| 483 | CH | O | H | $CO_2CH_3$ | $CH_3$ | H | H | H | |
| 484 | CH | O | H | $CO_2CH_3$ | $CF_3$ | H | H | H | |
| 485 | CH | O | H | $CO_2C_2H_5$ | $C_2H_5$ | H | H | H | |
| 486 | CH | O | H | $CO_2C_2H_5$ | n-$C_3H_7$ | H | H | H | |
| 487 | CH | O | H | $CONHCH_3$ | $CH_3$ | H | H | H | |
| 488 | CH | O | H | $CONHC_2H_5$ | $CH_3$ | H | H | H | |
| 489 | CH | O | H | $CON(CH_3)_2$ | $CH_3$ | H | H | H | |
| 490 | CH | O | H | $CH_3$ | $CO_2CH_3$ | H | H | H | |

*stands for melting point. ° C. is the unit.

The present invention also includes preparation of benzopyrone compounds and their isomers having general formula (I).

The compounds of formula I can be easily prepared by reaction of the benzylhalide having general formula (II) with benzopyrone compounds containing hydroxy group having general formula (III) under base condition according to the scheme I.

Scheme I:

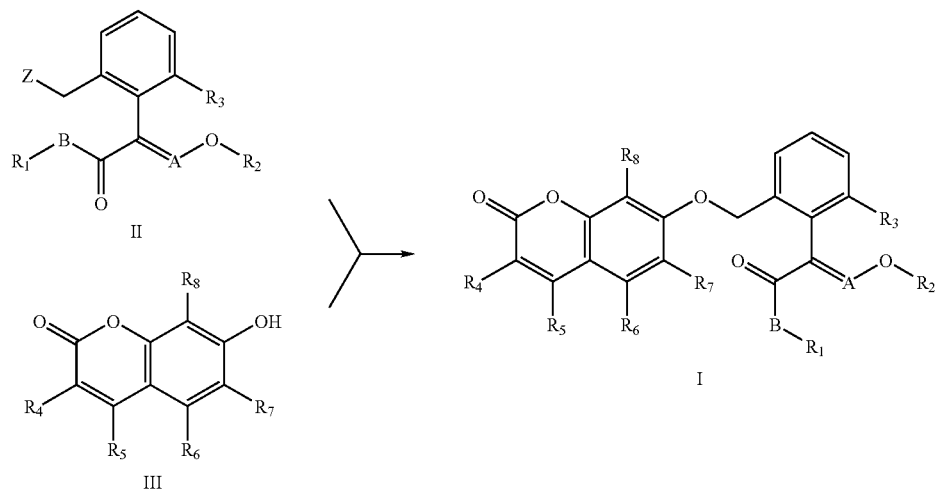

wherein: Z is leaving group, such as halogen (Cl, Br, or I). $R_1$, $R_2$, $R_3$, $R_4$, $R_5$, $R_6$, $R_7$, $R_8$, A, B, is as defined above.

Preparation condition of compounds having general formula (I): In proper solvent, hydroxylbenzopyrone compounds having general formula (III) are treated with proper base to become salts, then the compound having general formula (II) is added into the mixture, the reaction is carried out at proper temperature. After reaction is completed, the target compound I is obtained by normal way.

The proper solvent mentioned may be selected from the following ones, such as tetrahydrofuran, acetonitrile, toluene, xylene, benzene, DMF, DMSO, acetone or butanone and so on.

The proper base mentioned may be selected from the following ones, such as potassium hydroxide, sodium hydroxide, potassium carbonate, sodium carbonate, sodium bicarbonate, triethylamine, pyridine, pyridine or sodium hydride and so on.

The proper temperature mentioned is from room temperature to boiling point of solvent. Normal temperature is from 20 to 100° C.

The reaction may be finished in the course of 30 minutes-20 hours, generally 1-10 hours.

The reaction can be controlled by Thin-Layer Chromatography.

The intermediates of general formula (II) can be prepared according to the known methods, refer to U.S. Pat. No. 4,723,034 and U.S. Pat. No. 5,554,578.

Some of the hydroxylbenzopyrone compounds having general formula (III) are available from the chemical company, and are also prepared according to the methods reported in Journal of Medicinal Chemistry, 2001, 44 (5), 664-671, by the reaction $R_5COCHR_4CO_2CH_3(C_2H_5)$ with substituted resorcinol. Moreover, the compound may be straightly used to prepare the target compounds without further purification.

Some of the hydroxylbnezopyrone compounds having general formula (III) synthesized are showed in table 2.

TABLE 2

| III | $R_4$ | $R_5$ | $R_6$ | $R_7$ | $R_8$ | Physical property* |
|---|---|---|---|---|---|---|
| III-1 | H | $CH_3$ | H | H | $COCH_3$ | 158–160 |
| III-2 | H | $CH_3$ | H | H | $C(=NOMe)CH_3$ | 129–140 |
| III-3 | H | $H_3$ | H | H | $CO_2CH_3$ | 219–222 |
| III-4 | H | $CH_3$ | H | H | $CH_3$ | 256–258 |
| III-5 | Cl | $CH_3$ | H | H | H | 230–234 |
| III-6 | H | $CF_3$ | H | H | H | 180–183 |
| III-7 | $C_6H_5CH_2$ | $CH_3$ | H | H | H | 208–212 |
| III-8 | H | 4-F—$C_6H_4$ | H | H | H | 256–262 |
| III-9 | H | 3,4-$(MeO)_2C_6H_4$ | H | H | H | 184–188 |

TABLE 2-continued

| III | $R_4$ | $R_5$ | $R_6$ | $R_7$ | $R_8$ | Physical property* |
|---|---|---|---|---|---|---|
| III-10 | F | $CH_3$ | H | H | H | 203–206 |
| III-11 | H | $C_6H_5$ | H | H | H | 240–242 |
| III-12 | H | $C_6H_5$ | H | H | $CH_3$ | 260–262 |
| III-13 | Cl | $C_6H_5$ | H | H | H | 188–190 |
| III-14 | $CH_3$ | $CH_3$ | H | H | H | 118–120 |
| III-15 | $CH_3$ | $CH_3$ | H | H | $CH_3$ | 218–222 |
| III-16 | H | $n\text{-}C_3H_7$ | H | H | $CH_3$ | 176–178 |
| III-17 | Cl | $n\text{-}C_3H_7$ | H | H | H | 148–150 |
| III-18 | H | $i\text{-}C_3H_7$ | H | H | H | 160–162 |
| III-19 | $n\text{-}C_6H_{13}$ | $CH_3$ | H | H | H | 170–172 |
| III-20 | $i\text{-}C_3H_7CH_2CH_2$ | $CH_3$ | H | H | H | 101–102 |
| III-21 | $n\text{-}C_4H_9$ | $CH_3$ | H | H | H | 134–136 |
| III-22 | $n\text{-}C_3H_7$ | $CH_3$ | H | H | H | 142–144 |
| III-23 | H | $CH_2OCH_3$ | H | H | H | 186–190 |

*stands for melting point. ° C. is the unit.

The compounds of general formula (V) and (VII) can be easily prepared by reaction of the general formula (IV) and (VI), respectively, with methylamine aqueous solution.

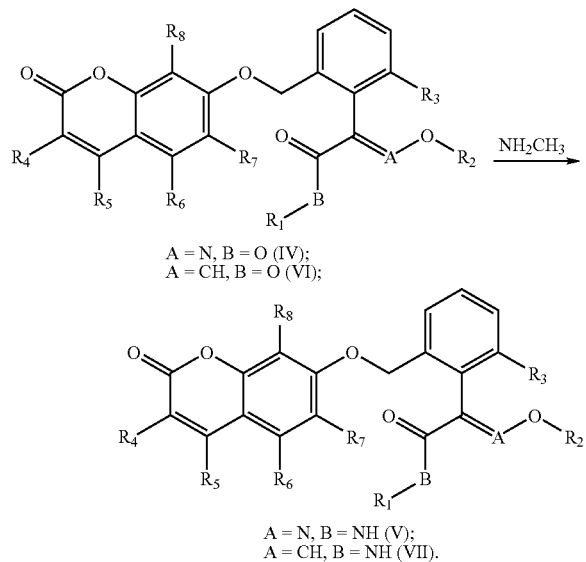

A = N, B = O (IV);
A = CH, B = O (VI);

A = N, B = NH (V);
A = CH, B = NH (VII).

The present invention also provides a composition of insecticides and fungicides. The active ingredients of the composition are the compounds having general formula (I), wherein the active ones being present in a total amount of 0.1 to 99% by weight, the rest being the acceptable carrier by agriculture.

The present invention, further more, provides preparation method of the said composition thereon. The compounds of general formula (I) and the carrier are mixed. The said composition may be a single component compound or mixture of compounds with several components.

The carrier in the invention accords to the requirements: it is easy to apply to the sites being to be treated for the carrier after it is confected with active component. For example, the sites could be plant, seed or soil convenient for store, transport or operation. The carrier could be solid or liquid, including the liquid which usually turns from gas condition under pressure. And the carriers which are used to confect insecticidal, bactericidal composition are applied.

Suitable solid carriers include natural and synthetic clays and silicates, for example diatomaceous earths, talcs, magnesium aluminium silicates, aluminium silicates(kaolin), montmorillonites and micas; calcium carbonate; calcium sulphate; ammonium sulphate; synthetic silicon oxides and synthetic calcium silicates or aluminium silicates; elements, for example carbon and sulphur; natural and synthetic resins, for example coumarone resins, polyvinyl chloride, and styrene polymers or copolymers; solid polychlorophenols; bitumen; waxes, beeswax or paraffin wax for instance.

Suitable liquid carriers include water, alcohols such as isopropanol or alcohol; ketones such as acetone, methyl ethyl ketone, methyl isopropy ketone or cyclohexanone; ethers; aromatics such as benzene, xylene, toluene; petroleum fractions such as kerosene or mineral oils, chlorinated aliphatic hydrocarbons such as carbon tetrachloride, tetrachloride ethylene or trichloride ethylene. Mixtures of these different liquids generally are often suitable.

The compositions of insecticides and fungicides are often formulated and transported in a concentrated form which is subsequently diluted by the user before application. The presence of small amounts of surfactant facilitates this process of dilution. Thus preferably at least one carrier in a composition according to the invention is a surfactant. For example the composition may contain at least two carriers, at least one of which is, a surfactant.

A surfactant may be an emulsifier, a dispersant or a wetting agent; it may be nonionic or ionic. Examples of suitable surfactant include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycol, sorbic alcohol, sucrose or pentaerythritol and condensations of these with ethylene oxide and/or propylene oxide; condensation products of fatty alcohol or alkyl phenols such as p-octylphenol or p-octylcresol, with ethylene-oxide and/or propylene oxide; sulphates or sulphonates of these condensation products; alkaline metal salts or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate.

Examples of compositions and formulations according to the invention are wettable powder, Dustable powder, granule and aqueous solution; emulsifiable concentrate, emulsion, suspension concentrate, aerosol composition and fumigant. Wettable powder usually contains 25, 50 or 75% weight (ab.w) of active ingredient and usually contain in addition to solid inert carrier, 3-10% w of a dispersant and, where necessary, 0-10% w of stabiliser(s) and/or other additives such as penetrants or stickers. Dustable powder are usually formulated as a dust concentrate having a similar composition to that of a wettable powder but a dispersant, and are diluted with further solid carrier to give a composition usually containing 0.5-10% weight of active ingredient. Granules are usually prepared to have a size between 10 and 100 BS mesh (1.676-0.152 mm), and may be manufactured by agglomeration or impregnation techniques. Generally, granules contain 0.5-75% w active ingredient and 0-10% weight of additives such as stabilisers, surfactants, slow release modifiers. The so-called "dry flowable powders" consist of relatively small granules having a relatively high concentration of active ingredient. Emulsifiable concentrates usually contain, in addition to a solvent and, when necessary, co-solvent, 1-50% weight /volume(ab. w/v) active ingredient, 2-20% w/v emulsifiers and 0-20% w/v of other additives such as stabilisers, penetrants and corrosion inhibitors. Suspension concentrates are usually contain 10-75% w active ingredient, 0.5-15% w of dispersing agents, 0.1-10% w of other additives such as defoamers, corrosion inhibitors, stabilisers, penetrants and stickers.

Aqueous dispersant and emulsions, for example compositions obtained by diluting a wettable powder or a concentrate according to the invention with water, also lie within the scope of the invention. The said emulsions may be of the water-in-oil or of the oil-in-water type.

The composition to which one or more other fungicides are added has wider spectrum activity than single compound having general formula (I). In addition, other fungicides may have synergistic effect on the fungicidal activity of the compound having general formula (I). The compound having general formula (I) can also be used with other insecticides, or with another fungicide and other insecticides simultaneously.

This invention has the following advantages:

The compounds of present invention have very good insecticide activity, and may be used to control insects such as armyworm, diamond backmoth, aphids, carmine spider mite, two-spotted spider mite, lady beetles, mites and culex mosquitoes, especially for lady beetles and culex mosquitoes. All these attributes are suitable for integrated insect management.

The compounds of present invention have wide spectrum fungicidal activity, and may be used to control diseases in all sorts of plants caused by by oomycete, basidiomycete, ascomycete pathogens, and it may also provide good control efficacy at very low rate because of the high activity. These compounds have penetration activity and can be used as soil and foliar fungicides. They can provide satisfied control of grape downy mildew, rice sheath blight, rice blast, tomato early blight, tomato late blight, wheat leaf rust, wheat leaf blotch, wheat powdery mildew, cucumber powdery mildew, cucumber downy mildew and cucumber grey mold

DESCRIPTION OF THE INVENTION IN DETAIL

The following examples are illustrative of the present invention.

PREPARATION EXAMPLE

Example 1

The Preparation of Compound 1

A reaction flask was charged a suspension of 60% sodium hydride 0.84 g (washed with petroleum ether), and then 30 ml of dry N,N-dimethylformamide (DMF) was added, the mixture was stirred at room temperature for 30 minutes. To this agitated suspension, 1.7 g of 7-hydroxycoumarin was added, the mixture was agitated continuously till to no gas emerging. 3.0 g of methyl (E)-α-[2-(bromomethyl)phenyl]-β-methoxyacrylate was added to the reaction mixture and they were agitated continuously for 3 hours at room temperature. The reaction mixture was poured into ice water, extracted with ethyl acetate 3 times. The combined extracts were washed with brine 3 times, dried, filtered and concentrated under vacuum, to obtain the crude oil product 5 g. This was subjected to column chromatography to obtain 2.8 g of compound 1 as a faint red-yellow oily substance in 76.5% yield.

$^1$HNMR(300 MHz, internal standard=TMS, CDCl$_3$): δppm 3.69 (3H, s), 3.88 (3H, s), 5.04 (2H, s), 6.19-6.23 (1H, d), 6.77 (1H, s), 6.83-6.87 (1H, d), 7.18-7.20 (1H, m), 7.26-7.34 (4H, m), 7.48-7.64 (2H, m).

Example 2

The Preparation of Compound 2

A reaction flask was charged a suspension of 60% sodium hydride 0.45 g (washed with petroleum ether), and then 20 ml of dry N,N-dimethylformamide (DMF) was added, the mixture was stirred at room temperature for 30 minutes. To this agitated suspension, 1.0 g of 7-hydroxy-4-methylcoumarin was added, the mixture was agitated continuously till to no gas emerging. 1.66 g of methyl (E)-α-[2-(chloromethyl)phenyl]-β-methoxyacrylate was added to the reaction mixture and they were agitated continuously for 3 hours at room temperature. The reaction mixture was poured into ice water, extracted with ethyl acetate 3 times. The combined extracts were washed with brine 3 times. Dried, filtered and concentrated, to obtain the crude product, as a yellow solid substance. This was subjected to column chromatography, using a 1:2 mixture of ethyl acetate and petroleum ether as the eluting solution to obtain 1.73 g of compound 2, with melting point of 140-143° C. in 80% yield.

$^1$HNMR(300 MHz, internal standard=TMS, CDCl$_3$): δppm 2.38 (3H, s), 3.74 (3H, s), 3.89 (3H, s), 5.04 (2H, s), 6.11 (1H, s), 6.77 (1H, s), 6.85-6.89 (1H, d), 7.17-7.20 (1H, m), 7.32-7.35 (2H, m), 7.49-7.52 (2H, m), 7.64 (1H, s).

Example 3

The Preparation of Compound 101

A reaction flask was added 1.2 g of K$_2$CO$_3$, 1.0 g of 7-hydroxy-4-methylcoumarin, 1.70 g of methyl (E)-2-(bromomethyl)-α-(methoxyimino)benzeneacetate and 20 ml Butanone, the reaction mixture was refluxed and agitated continuously for 5 hours. The reaction mixture was poured into ice water, extracted with ethyl acetate 3 times. The combined extracts were washed with brine 3 times, dried, filtered and concentrated under vacuum, to obtain the crude product, as a yellow solid substance. This was subjected to column chromatography, using a 1:2 mixture of ethyl acetate and petroleum ether as the eluting solution to obtain 1.77 g of compound 101, with melting point of 150-152° C. in 83% yield.

¹HNMR(300 MHz, internal standard=TMS, CDCl₃): δppm 2.39 (3H, s), 3.87 (3H, s), 4.05 (3H, s), 5.02 (2H, s), 6.13 (1H, s), 6.80-6.86 (2H, m), 7.23-7.26 (1H, m), 7.43-7.49 (4H, m).

Example 4

The Preparation of Compound 153

A reaction flask was added 0.27 g of compound 101, more than two fold(mol)methylamine and 30 ml methanol, the reaction mixture was continuously agitated overnight, then concentrated and extracted with ethyl acetate 2 times. The combined extracts were washed with water 3 times and then washed with brine 2 times, dried, filtered and concentrated, to obtain 0.24 g of compound 153, with melting point of 210-214° C. in 89% yield.

¹HNMR(300 MHz, internal standard=TMS, CDCl₃): δppm 2.38 (3H, s), 2.91-2.93 (3H, d), 3.97 (3H, s), 5.02 (2H, s), 6.13 (1H, s), 6.82-6.87 (3H, m), 7.23 (1H, d), 7.39-7.50 (4H, m).

The preparation of other compounds, please refers to the way as above. ¹HNMR of other compounds are provided as follows (300 MHz, internal standard=TMS, CDCl₃):

Compound 3: δppm 2.36 (3H, s), 2.37 (3H, s), 3.72 (3H, s), 3.84 (3H, s), 5.09 (2H, s), 6.13 (1H, s), 6.75-6.78 (1H, d), 7.18-7.21 (1H, m), 7.34-7.36 (3H, m), 7.50-7.52 (1H, m)7.61 (1H, s).

Compound 4: δppm 2.41 (3H, s), 3.69 (3H, s), 3.81 (3H, s), 5.08 (2H, s), 6.20 (1H, s), 6.68-6.71 (1H, d), 7.18-7.21 (4H, m), 7.32-7.50 (5H, m), 7.59 (1H, s), 7.92 (1H, m).

Compound 5: δppm 2.17 (3H, s), 2.35 (3H, s), 3.73 (3H, s), 3.88 (3H, s), 5.02 (2H, s), 6.78 (1H, s), 6.83-6.85 (1H, d), 7.31-7.34 (3H, m), 7.45-7.47 (2H, d), 7.62 (1H, s).

Compound 6: δppm 2.32 (3H, s), 2.31-2.36 (6H, d), 3.69 (3H, s), 3.84 (3H, s), 5.07 (2H, s), 6.74-6.77 (1H, d), 7.17-7.20 (1H, m), 7.31-7.36 (3H, m), 7.51-7.54 (1H, m), 7.61 (1H, s).

Compound 12: δppm 2.53 (3H, s), 3.74 (3H, s), 3.89 (3H, s), 5.04 (2H, s), 6.78 (1H, s), 6.83-6.85 (1H, d), 7.18-7.21 (1H, m), 7.32-7.35 (2H, m), 7.47-7.50 (2H, d), 7.64 (1H, s).

Compound 17: δppm 1.25-1.32 (3H, m), 2.36 (3H, s), 2.74-2.76 (2H, m), 3.71 (3H, s), 3.84 (3H, s), 5.08 (2H, s), 6.15 (1H, s), 6.75-6.78 (1H, d), 7.18-7.21 (1H, m), 7.33-7.38 (3H, m), 7.50-7.54 (1H, m), 7.61 (1H, s).

Compound 18: δppm 1.10-1.15 (3H, t), 2.37 (3H, s), 2.60-2.68 (2H, q), 3.74 (3H, s), 3.89 (3H, s), 5.03 (2H, s), 6.76 (1H, d), 6.84-6.88 (1H, dd), 7.18-7.21 (1H, m), 7.32-7.35 (2H, m), 7.45-7.53 (2H, m), 7.63 (1H, s).

Compound 19: δppm 3.48 (3H, s), 3.74 (3H, s), 3.89 (3H, s), 4.56 (2H, s), 5.04 (2H, s), 6.34 (1H, s), 6.79 (1H, d), 6.84-6.88 (1H, dd), 7.18-7.21 (1H, m), 7.30-7.36 (2H, m), 7.41-7.44 (1H, d), 7.48-7.51 (1H, m), 7.64 (1H, s).

Compound 24: δppm 3.72 (3H, s), 3.92 (3H, s), 5.10 (2H, s), 6.78 (1H, s), 6.94-7.21 (1H, d), 7.22 (1H, m), 7.33-7.35 (2H, m), 7.36-7.45 (2H, m), 7.66 (1H, s), 8.13 (1H, s).

Compound 25: δppm 2.36 (3H, d), 2.62 (3H, d), 3.71 (3H, s), 3.84 (3H, s), 5.09 (2H, s), 6.82 (1H, d), 7.19-7.21 (1H, m), 7.33-7.35 (3H, m), 7.36-7.37 (1H, m), 7.61 (1H, s).

Compound 26: δppm 1.25-1.30 (6H, m), 3.20-3.23 (1H, m), 3.74 (3H, s), 3.91 (3H, s), 5.04 (2H, s), 6.15 (1H, s), 6.790-6.799 (1H, d), 6.80-6.90 (1H, m), 7.18-7.23 (1H, m), 7.32-7.37 (2H, m), 7.48-7.57 (2H, m), 7.64 (1H, s).

Compound 27: δppm 0.95-1.00 (3H, t), 1.58 (2H, m), 2.36 (3H, s), 2.58 (2H, t), 3.73 (3H, s), 3.89 (3H, s), 5.02 (2H, s), 6.75 (1H, d), 6.84-6.88 (1H, dd), -7.18 (1H, m), 7.31-7.34 (1H, m), 7.47-7.51 (2H, m), 7.63 (1H, s).

Compound 29: δppm 3.74 (3H, s), 3.90 (3H, s), 5.06 (2H, s, ), 6.17 (1H, s), 6.80-6.85 (2H, m), 7.24-7.26 (1H, m), 7.28-7.35 (5H, m), 7.38-7.51 (3H, m), 7.66 (1H, s).

Compound 32: δppm 3.73 (3H, s), 3.90 (3H, s), 5.05 (2H, s), 6.75-6.78 (1H, dd), 6.84-6.85 (1H, d), 6.94-6.98 (1H, d), 7.19-7.21 (1H, m), 7.30-7.35 (4H, m), 7.53-7.55 (4H, m), 7.65 (1H, s).

Compound 33: δppm 1.27-1.32 (3H, m), 2.74-2.77 (2H, m), 3.74 (3H, s), 3.89 (3H, s), 5.04 (2H, s), 6.13 (1H, s), 6.78-6.79 (1H, d), 6.85-6.89 (1H, m), 7.18-7.21 (1H, m), 7.32-7.35 (2H, m), 7.48-7.52 (2H, m), 7.64 (1H, s).

Compound 34: δppm 0.90-1.03 (3H, m), 1.67-1.72 (2H, m), 2.65-2.70 (2H, m), 3.73 (3H, s), 3.89 (3H, s), 5.04 (2H, s), 6.10 (1H, s), 6.78-6.79 (1H, d), 6.85-6.89 (1H, m), 7.19-7.21 (1H, m), 7.33-7.35 (2H, m), 7.47-7.51 (2H, m), 7.64 (1H, s).

Compound 35: δppm 1.00-1.25 (3H, m), 1.69-1.72 (2H, m), 2.36 (3H, s), 2.65-2.70 (2H, m), 3.71 (3H, s), 3.84 (3H, s), 5.08 (2H, s), 6.12 (1H, s), 6.75-6.78 (1H, d), 7.21-7.26 (1H, m), 7.33-7.38 (3H, m), 7.50-7.53 (1H, m), 7.61 (1H, s).

Compound 36: δppm 0.97 (3H, t), 1.66 (2H, m), 2.67 (3H, s), 3.74 (3H, s), 3.89 (3H, s), 5.04 (2H, s), 6.78 (1H, d), 6.85-6.88 (1H, dd), 7.22 (1H, m), 7.33-7.35 (2H, m), 7.46-7.49 (2H, m), 7.64 (1H, s).

Compound 37: δppm 1.05 (3H, m), 1.57-1.64 (2H, m), 2.16 (3H, s), 2.71-2.76 (2H, t), 3.70 (3H, s), 3.83 (3H, s), 5.02 (2H, s), 6.78 (1H, d), 6.87 (1H, m), 7.20 (1H, m), 7.32 (2H, m), 7.45 (2H, m), 7.64 (1H, s).

Compound 38: δppm(DMSO-d₆) 3.65 (3H, s), 3.88 (3H, s), 5.03 (2H, s), -6.15 (1H, s), 6.83-6.87 (1H, dd), 6.91 (1H, d), 7.09-7.17 (2H, m), 7.23-7.35 (4H, m), 7.43-7.46 (1H, m), 7.51-7.55 (2H, m), 7.66 (1H, s).

Compound 41: δppm 3.74 (3H, s), 3.91 (3H, s), 5.06 (2H, s), 6.20 (1H, s), 6.86 (2H, m), 7.22 (2H, m), 7.33-7.36 (2H, m), 7.56 (3H, m), 7.66 (1H, s), 7.77 (2H, d). Compound 50: δppm 2.34 (3H, s), 3.74 (3H, s), 3.89 (3H, s), 5.04 (2H, s), 6.78-6.79 (1H, d), 6.92-6.96 (1H, dd), 7.18-7.21 (1H, m), 7.32-7.35 (2H, m), 7.41-7.44 (1H, d), 7.48-7.51 (1H, m), 7.65 (1H, s).

Compound 52: δppm 3.74 (3H, s), 3.90 (3H, s), 5.06 (2H, s), 6.20 (1H, s), 6.80-6.86 (1H, m), 7.18-7.22 (1H, m), 7.32-7.37 (4H, m), 7.41-7.44 (2H, m), 7.50-7.52 (4H, m), 7.65 (1H, s).

Compound 58: δppm 3.74 (3H, s), 3.91 (6H, d), 3.96 (3H, s), 5.06 (2H, s), 6.19 (1H, s), 6.81-6.82 (1H, m), .6.85 (1H, s), 6.93-7.04 (3H, m), 7.19-7.22 (1H, m), 7.33-7.36 (2H, m), 7.44-7.52 (2H, m), 7.66 (11H, s).

Compound 68: δppm(DMSO-d₆) 2.49 (3H, s), 3.66 (3H, s), 3.89 (3H, s), 3.92 (2H, s), 5.00 (2H, s), 6.78-6.79 (1H, d), 6.85-6.89 (1H, dd), 7.10-7.22 (6H, m), 7.26-7.29 (2H, m), 7.42 (1H, m), 7.61-7.66 (2H, m).

Compound 100: δppm 2.54 (3H, s), 3.87 (3H, s), 4.04 (3H, s), 5.02 (2H, s), 6.81-6.85 (1H, s), 7.26 (1H, d), 7.43-7.52 (5H, m).

Compound 102: δppm 2.32 (3H, s), 2.37 (3H, s), 3.84 (3H, s), 4.03 (3H, s), 5.05 (2H, s), 6.13 (1H, s), 6.76-6.79 (1H, d), 7.26 (1H, d), 7.34-7.43 (3H, m), 7.45-7.46 (1H, d).

Compound 103: δppm 2.18 (3H, s), 2.37 (3H, s), 3.91 (3H, s), 3.98 (3H, s), 5.35 (2H, s), 6.85 (1H, s), 6.86-6.88 (1H, d), 7.26-7.40 (3H, m), 7.49-7.52 (1H, d), 7.62-7.65 (1H, d).

Compound 104: δppm 2.17 (3H, s), 2.35 (3H, s), 3.86 (3H, s), 4.04 (3H, s), 5.00 (2H, s), 6.78-6.85 (2H, m), 7.20-7.25 (1H, d), 7.40-7.61 (4H, m).

Compound 109: δppm 2.91-2.93 (3H, d), 3.97 (3H, s), 5.02 (2H, s), 6.23-6.26 (1H, d), 6.82-6.86 (3H, m), 7.20-7.23 (1H, m), 7.34-7.37 (1H, d), 7.39-7.45 (2H, m), 7.50-7.53 (1H, m), 7.61-7.64 (1H, d).

Compound 111: δppm 3.87 (3H, s), 4.05 (3H, s), 5.02 (2H, s), 6.23-6.26 (1H, d), 6.79-6.85 (2H, m), 7.21 (1H, d), 7.34-7.37 (1H, d), 7.41-7.45 (2H, m), 7.47-7.53 (1H, m), 7.61-7.64 (1H, d).

Compound 401: δppm 1.32-1.36 (6H, m), 2.39 (3H, s), 3.27 (1H, m), 3.74 (3H, s), 3.89 (3H, s), 5.03 (2H, s), 6.72-6.73 (1H, d), 6.83-6.87 (1H, dd), 7.17-7.20 (1H, m), 7.31-7.34 (2H, m), 7.46-7.52 (2H, m), 7.63 (1H, s).

Compound 402: δppm 0.93 (3H, m), 1.45 (4H, m), 2.35 (3H, s), 2.60 (2H, t), 3.74 (3H, s), 3.89 (3H, s), 5.04 (2H, s), 6.78 (1H, d), 6.84-6.85 (1H, m), 7.18-7.20 (1H, m), 7.30-7.35 (2H, m), 7.45-7.50 (2H, d), 7.64 (1H, s).

Compound 404: δppm 1.25 (6H, m), 1.39 (2H, m), 1.63 (1H, m), 2.39 (3H, s), 2.62 (2H, t), 3.72 (3H, s), 3.86 (3H, s), 5.01 (2H, s), 6.78 (1H, d), 6.84 (1H, m), 7.20 (1H, m), 7.32 (2H, m), 7.45 (2H, d), 7.64 (1H, s).

Compound 405: δppm 0.88 (3H, t), 1.42-1.52 (8H, m), 2.38 (3H, s), 2.64 (2H, t), 3.72 (3H, s), 3.86 (3H, s), 5.01 (2H, s), 6.78 (1H, d), 6.84 (1H, m), 7.20 (1H, m), 7.32 (2H, m), 7.45 (2H, d), 7.64 (1H, s).

Compound 408: δppm 2.37 (3H, s), 3.2-3.6 (1H, m), 3.72 (3H, s), 3.85 (3H, s), 5.09 (2H, s), 6.18 (1H, s), 6.76-6.79 (1H, d), 7.18-7.21 (1H, m), 7.34-7.43 (3H, m), 7.51-7.54 (1H, m), 7.68 (1H, 5).

Compound 409: δppm 0.96-1.03 (6H, m), 1.58-1.63 (4H, m), 2.71-2.79 (4H, m), 3.72 (3H, s), 3.85 (3H, s), 5.00 (2H, s), 6.79 (1H, d), 6.87 (1H, m), 7.19 (1H, m), 7.32 (2H, m), 7.45 (2H, m), 7.64 (1H, s).

Compound 410: δppm 0.86-0.88 (3H, m), 1.68-1.75 (2H, m), 2.66-2.71 (2H, m), 3.87 (3H, s), 4.05 (3H, s), 5.02 (2H, s), 6.80-6.92 (3H, m), 7.21-7.26 (1H, d), 7.39-7.69 (3H, m).

Compound 411: δppm 3.87 (3H, s), 4.05 (3H, s), 5.02 (2H, s), 6.73-6.77 (1H, m), 6.87-6.88 (1H, d), 6.97-7.00 (1H, d), 7.21-7.24 (1H, m), 7.28-7.32 (2H, m), 7.42-7.57 (6H, m).

Compound 412: δppm 0.94 (3H, t), 1.46 (2H, m), 2.35 (3H, s), 2.60 (2H, t), 3.74 (3H, s), 3.89 (3H, s), 5.04 (2H, s), 6.78 (1H, d), 6.84 (1H, m), 7.20 (1H, m), 7.32 (2H, m), 7.42-7.45 (2H, d), 7.64 (1H, s).

Compound 413: δppm 0.94 (3H, m), 1.45 (4H, m), 2.36 (3H, s), 2.60 (2H, t), 3.86 (3H, s), 4.05 (3H, s), 5.00 (2H, s), 6.78 (1H, d), 6.84 (1H, m), 7.20 (1H, m), 7.38-7.45 (4H, m).

Compound 414: δppm 0.88 (3H, m), 1.48-1.65 (8H, m), 2.36 (3H, s), 2.62 (2H, t), 3.86 (3H, s), 4.05 (3H, s), 5.00 (2H,.s), 6.85 (1H, m), 6.84 (1H, m), 7.20 (1H, m), 7.39-7.45 (4H, m).

Formulation Example (Weight/Weight %)

Example 5

60% Wettable Powder

| | |
|---|---|
| Compound 6 | 60% |
| Sodium dodecylnaphthalenesulfate | 2% |
| Sodium lignosulphonate | 9% |
| Kaolin | complement to 100% |

All the solid components are well mixed and shattered until the particle size of the active ingredient reaches the standard in order to obtain 60% wettable powder.

Example 6

35% Emulsion Concentrate

| | |
|---|---|
| Compound 1 | 35% |
| Phosphorous acid | 10% |
| Ethylenoxy aliphatic acid glycerin ester | 15% |
| Cyclohexanone | complement to 100% |

Phosphorous acid is dissolved in cyclohexanone, then the compound 1 and ethylenoxy aliphatic acid glycerin ester are added, a emulsifiable concentrate in transparent solution is obtained finally.

Example 7

30% Aqueous Suspension Concentrate

| | |
|---|---|
| Compound 25 | 30% |
| Sodium dodecylnaphthalenesulfate | 4% |
| Hemicellulose | 2% |
| Epoxypropane | 8% |
| Water | complement to 100% |

The mixture of compound 25, 80% of the amount of water should being added and sodium dodecylnaphthalenesulfate are shattered in a mill (1 mm ball). Other components are dissolved in the rest water, and are added under stirring.

Example 8
25% Suspension Emulsifier

| | |
|---|---|
| Compound 12 | 25% |
| Alkylsulphonates (emulsifier 1) | 4% |
| Ethylenoxy aliphatic acid glycerin ester (emulsifier 2) | 2% |
| Calcium dodecylbenzenesulfate (emulsifier 3) | 1.5% |
| Polyethylenoxyalkyl propyl ether (dispersant) | 2.5% |
| Cyclohexanone (solvent 1) | 30% |
| Petroleum fractions (boiling point >200° C.) (solvent 2) | complement to 100% |

Compound 12 is dissolved in 80% of the amount of solvent should being added, and then emulsifiers and dispersant are added, the mixture is stirred completely and shattered in a mill(1 mm ball). Other solvents are added.

Test of Biological Activity

Example 9
Fungicidal Activity Determination

Determination of fungicidal activities against plant diseases of selected compounds were carried out by following procedure:

Plants were prepared in pot. Technical samples were dissolved in DMF and diluted to required concentration by water. Test solution was sprayed onto potted plant. Pathogen inoculation was carried out after 24 hours then plants were hold in growth chambers containing constant temperature and moisture for effect. When untreated plant was under desirable disease severity (after 1 week approximately), assessment was carried out by visual observation.

Part of test results:

At 200 ppm, compound 1, 2, 4, 5, 6, 12, 18, 19, 25, 26, 33, 34, 35, 37, 50, 52, 58, 69, 109, 402, 405, 409, 410, 413, 414 showed 100% control against cucumber downy mildew, while compound 3, 24, 36, 38, 153, 411 showed >95% control.

At 200 ppm, compound 2, 6, 18, 50, 58, 100, 402 showed 100% control against cucumber grey mold, while 6, 101, 102, 103, 106, 412 showed >75% control.

At 200 ppm, compound 6, 7, 10 showed 100% against grape downy mildew, while 8, 106, 154 showed >85% control.

At 200 ppm, compound 3, 101 showed >85% control against rice sheath blight.

At 200 ppm, compound 6, 8, 10 showed >85% control against rice blast.

At 200 ppm, compound 402, 412, 413 showed 100% control against wheat powdery mildew, while 9, 101, 111, 410 showed >70% control.

At 200 ppm, compound 6 showed 100% control against wheat leaf rust, while 7, 10 showed >95% control and 8, 154 showed >75% control.

At 200 ppm, compound 6>90% and compound 7, 8, 9, 10, 11, 154 showed >80% control against wheat leaf blotch.

At 200 ppm, compound 6, 7 showed >100% control against tomato early stage blight, while 8, 10 showed >90% control, while 11 showed >75% control.

At 200 ppm, compound 6 showed >95% control against tomato late blight, while 10 showed >75% control.

At 200 ppm, compound 5, 6 showed >95% control against corn leaf blight. Comparing with the compound JP51 in JP04-182461, the part of test results of some compounds activity against cucumber downy mildew refers to table 3.

>50% control of army worm, diamond backmoth and green peach aphid.

At 300 ppm, compound 7, 9, 10 showed 100% control of Mexican lady beetle, while compound 7 showed >50% control of two-spotted spider mite.

What is claimed:

1. A benzopyrone compound having the general formula (I):

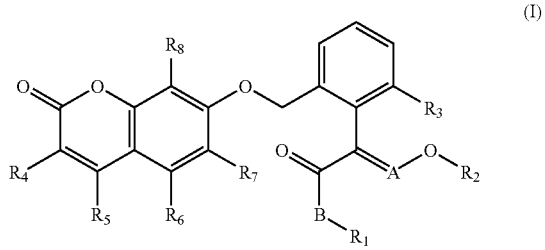

wherein:

A is CH;

B is O;

$R_1$, $R_2$, and $R_5$ are methyl;

$R_3$, $R_6$, $R_7$, and $R_8$ are H;

$R_4$ is methyl or n-butyl.

2. A method of controlling insects which comprises applying the compound according to claim 1 to a plant.

TABLE 3

| Comparision of fungicidal activity against cucumber downy mildew (50 ppm) | | | | | | | | | | | | | |
|---|---|---|---|---|---|---|---|---|---|---|---|---|
| Compound | | | | | | | | | | | | | |
| | 1 | 2 | 5 | 6 | 12 | 26 | 37 | 52 | 402 | 405 | 409 | 141 | JP51 |
| control(%) | 100 | 100 | 100 | 100 | 100 | 100 | 100 | 100 | 100 | 100 | 100 | 100 | 20 |

Example 10

Determination of Insecticidal/Acaricidal Activity

Numerous insect larvae were put into containers then were fed with treated corn leaves. Potter's spraying tower was used as the sprayer and spraying volume was 1 mL. The spraying pressure was 13.5 lb/in².

Test Result:

At 10 ppm, compound 2, 5, 6 showed 100% control of culex mosquitoes. At 600 ppm, compound 5 and 6 showed 3. A method of controlling fungi which comprises applying the compound according to claim 1 to a plant.

4. A fungicidal or insecticidal composition comprising the compound of claim 1 as an active ingredient, wherein the weight percentage of the active ingredient in the composition is from 0.1 to 99%.

* * * * *